United States Patent
Parks et al.

(10) Patent No.: US 10,827,995 B2
(45) Date of Patent: Nov. 10, 2020

(54) SYSTEM AND METHOD FOR SPATIOTEMPORALLY SYNCHRONIZING AND DISPLAYING BODILY ORGAN IMAGES AND PHYSIOLOGICAL PARAMETER(S) RELATED THERETO

(71) Applicant: GIVEN IMAGING LTD., Yoqneam (IL)

(72) Inventors: Thomas R. Parks, Hermosa Beach, CA (US); Sanket Khandelwal, Culver City, CA (US); Sergiy Kanilo, Los Angeles, CA (US)

(73) Assignee: GIVEN IMAGING LTD., Yoqneam (IL)

( * ) Notice: Subject to any disclaimer, the term of this patent is extended or adjusted under 35 U.S.C. 154(b) by 1594 days.

(21) Appl. No.: 14/409,601

(22) PCT Filed: Jun. 20, 2013

(86) PCT No.: PCT/IL2013/050530
§ 371 (c)(1),
(2) Date: Dec. 19, 2014

(87) PCT Pub. No.: WO2013/190557
PCT Pub. Date: Dec. 27, 2013

(65) Prior Publication Data
US 2015/0173697 A1    Jun. 25, 2015

Related U.S. Application Data

(60) Provisional application No. 61/662,562, filed on Jun. 21, 2012.

(51) Int. Cl.
*A61B 6/00* (2006.01)
*A61B 6/12* (2006.01)
(Continued)

(52) U.S. Cl.
CPC ............... *A61B 6/463* (2013.01); *A61B 5/01* (2013.01); *A61B 5/04884* (2013.01);
(Continued)

(58) Field of Classification Search
CPC ......... A61B 6/463; A61B 6/469; A61B 6/487; A61B 6/12; A61B 6/4266; A61B 6/48;
(Continued)

(56) References Cited

U.S. PATENT DOCUMENTS

2002/0115931 A1   8/2002   Strauss
2009/0257554 A1   10/2009  Parks

OTHER PUBLICATIONS

International Search Report for International Application No. PCT/IL2013/050530, dated Oct. 25, 2013.

*Primary Examiner* — Peter Luong
(74) *Attorney, Agent, or Firm* — Pearl Cohen Zedek Latzer Baratz LLP

(57) ABSTRACT

A visualization system may include a radiographic imaging apparatus for obtaining radioscopic images of a bodily organ with one or more radio discernible sensors introduced into the organ in order to sense physiological parameter(s) related to the physiological activity of the imaged organ. The sensors may be pressure sensors, temperature sensors, etc. The visualization system may also include a computing device for identifying the organ and the relative locations of the sensors in each radioscopic image, and it may generate a displayable representation symbol that may represent the sensors and the sensors' output values. Display attributes that depend on the sensors' locations and output values may define the location of the representation symbol. Acquiring a radioscopic image of the bodily organ and reading the sensors' outputs may be performed simultaneously in order to facilitate spatiotemporal synchronization between display of the image of the organ and display of the representation symbol.

20 Claims, 19 Drawing Sheets

(51) Int. Cl.
  *A61B 5/01* (2006.01)
  *A61B 5/0488* (2006.01)
  *A61B 5/053* (2006.01)
  *A61B 5/145* (2006.01)
  *G06T 11/60* (2006.01)
  *A61B 90/00* (2016.01)

(52) U.S. Cl.
  CPC ........ A61B 5/0538 (2013.01); A61B 5/14539 (2013.01); A61B 5/14542 (2013.01); A61B 5/14546 (2013.01); A61B 6/12 (2013.01); A61B 6/4266 (2013.01); A61B 6/469 (2013.01); A61B 6/487 (2013.01); G06T 11/60 (2013.01); *A61B 2090/397* (2016.02); *G06T 2210/41* (2013.01)

(58) Field of Classification Search
  CPC .............. A61B 5/14539; A61B 5/0538; A61B 5/14546; A61B 5/14542; A61B 5/01; A61B 90/39; A61B 2090/397; G06T 11/60; G06T 2210/41
  See application file for complete search history.

Fig. 3A

| Sensor No. | Sensor Location | Sensor Output [V] | Graphical Object Attributes | |
|---|---|---|---|---|
| | | | Location | Radius, R[mm] |
| 1 | {89, 224} | 9.4 | {89, 224} | 4.95 |
| 2 | {95, 185} | 8.1 | {95, 185} | 4.10 |
| 3 | {43, 224} | 6.3 | {43, 224} | 3.30 |
| ≡ | ≡ | ≡ | ≡ | ≡ |

| Sensor No. | Sensor Location | Sensor Output [V] | Graphical Object Attributes | | |
|---|---|---|---|---|---|
| | | | Location | Color, C | Orientation, φ [degrees] |
| 1 | {89, 224} | 9.4 | {89, 224} | Red | 0 |
| 2 | {95, 185} | 8.1 | {95, 185} | Reddish | +10 |
| 3 | {43, 224} | 6.3 | {43, 224} | Orange | +12 |
| ≡ | ≡ | ≡ | ≡ | ≡ | ≡ |

330, 340, 350

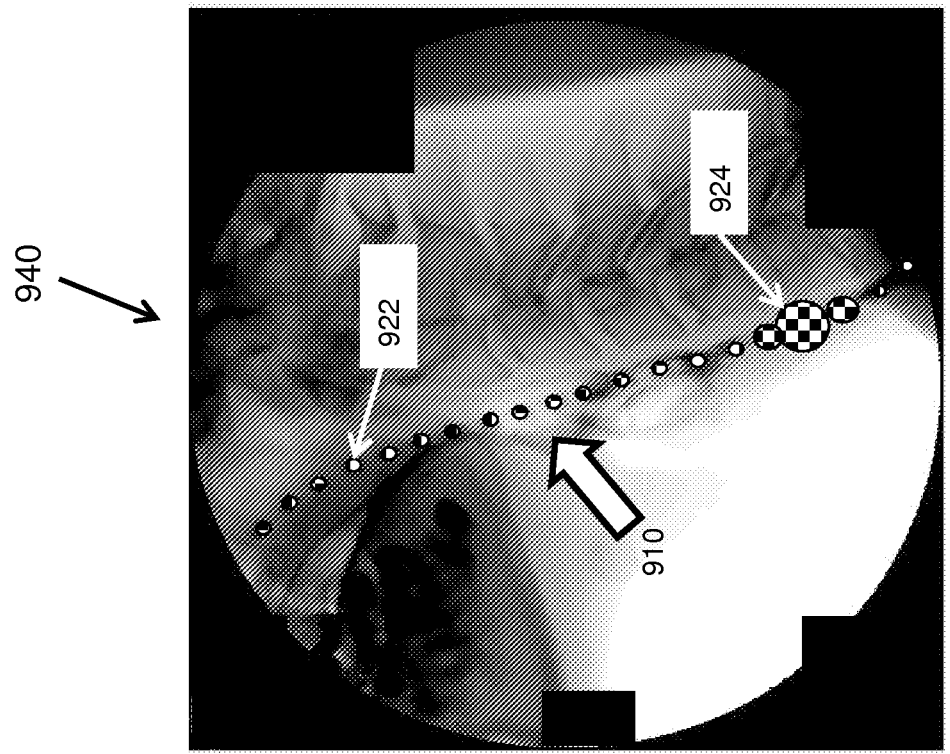
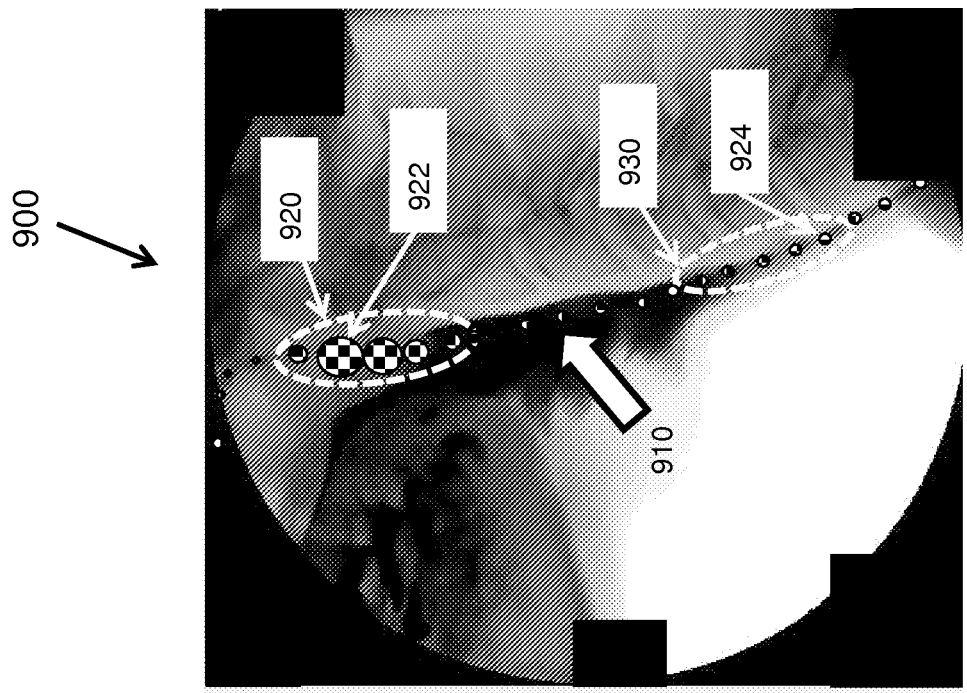

SYSTEM AND METHOD FOR SPATIOTEMPORALLY SYNCHRONIZING AND DISPLAYING BODILY ORGAN IMAGES AND PHYSIOLOGICAL PARAMETER(S) RELATED THERETO

CROSS-REFERENCE TO RELATED APPLICATIONS

This application is a National Phase Application of PCT International Application No. PCT/IL2013/050530, International Filing Date Jun. 20, 2013, claiming priority of U.S. Provisional Patent Application No. 61/662,562, filed Jun. 21, 2012, which is hereby incorporated by reference.

FIELD OF THE INVENTION

The present invention generally relates to an imaging system and more specifically to a method for spatiotemporally synchronizing between display of images of a bodily organ (e.g., the throat, organs of the gastrointestinal ("GI") tract, blood vessel, etc.) and display of one or more physiological parameters (e.g., peristaltic pressure, temperature, acidity (pH), etc.) related to the displayed bodily organ, and to a visualization and analysis system that uses the display method.

BACKGROUND

A variety of medical imaging technologies is available for producing images of the interior of the human body, for example for diagnostic purpose. Radiography is frequently used for this purpose, and fluoroscopy is an imaging technique used by physicians/radiologists to obtain real-time moving image of internal organs or structures of a patient (e.g., small bowel, colon, anorectum, or other parts of the GI system, blood vessel, etc.) through the use of a fluoroscope. Such images are typically used during surgeries, for example in order to ensure that a stent or screw is inserted correctly.

There are conventional imaging systems, one of which is described in U.S. Patent Publication No. 2009/0257554, that use a contrast material to visualize and display bodily organs or structures, and that can also measure and display physiological parameters (e.g., peristaltic pressure) that pertain to the visualized bodily organ. However, these conventional systems display the physiological parameters (e.g., as a pressure curve) alongside an image of the bodily organ, and atop an illustration of the imaged bodily organ. This display method, whereby organ images and their physiological parameters are displayed side-by-side, is inconvenient because the radiologist/physician's attention is drawn to two, spaced apart, locations on the display monitor—one where the image of the organ is displayed, and another where the physiological parameter is displayed. In addition, since the physiological parameter is displayed on top of an illustration of the involved organ, part of the radiologist/physician's task is to associate parameter values (e.g., peristaltic pressure values) with the correct locations on the imaged organ/structure, and this is rather inconvenient.

SUMMARY

A visualization system may include a radioscopic imaging apparatus for obtaining radioscopic images of a bodily organ/structure (e.g., swallowing system, GI tract; e.g., esophagus, small bowel, colon, anorectum, cardiac system, blood vessel, etc.) with a sensing element that may be positioned beforehand in or adjacent to the organ in order to sense a physiological parameter (e.g., pressure, acidity (pH), temperature, impedance, capacitance, Electromyography (EMG), Oxygen saturation, density of a blood constituent, etc.) that may be related or pertain to, or may result from the physiological activity of, the imaged organ. The sensing element may include one or more radio discernible sensors (e.g., radiopaque sensors). By 'radio discernible sensor' is meant a sensor (e.g., pressure sensor) that is made of or includes (e.g., by being coated by a layer of) a material that makes the sensor visually or otherwise discernible in a radioscopic image. The sensing element may include radio discernible sensors of the same type in order to sense one physiological parameter (e.g.; peristaltic pressure), or of different types in order to sense two or more physiological parameters (e.g.; peristaltic pressure and acidity (pH)). For example, all of the sensors may be pressure sensors, or temperature sensors, etc., or some sensors may be pressure sensors (for example) and other sensors may be temperature sensors (for example), etc.

The visualization system may also include a computing device for identifying an image of the organ and sensors in radioscopic images. The terms 'radioscopic image' and 'image' are used herein interchangeably. If a sensor cannot be identified in a particular image (e.g., due to it being radio-wise indiscernible), its location may be determined based on, or it may be inferred from other sensors whose locations can be identified in that particular image and/or in other images, or by using one or more radio discernible markers that may be embedded into the sensor itself, or into an instrument (e.g., catheter) that may be used to insert the sensor or to set it in place. (A sensor location may be inferred by, for example, using interpolation or extrapolation.)

The computing device may generate a displayable representation symbol that may represent, correspond to, or be in line with the sensors' locations and output values. The displayable representation symbol may include a displayable graphical element for each sensor regardless of whether the sensor location in the image is identified in a radioscopic image or inferred. The graphical elements forming a displayable representation symbol may be constructed as one graphical object or individually, as separate graphical objects.

With each graphical element may be associated display attributes. The display attributes may define the location of the graphical element relative to a displayed radioscopic image of the bodily organ, and the visual appearance of the graphical element. The values of the display attributes of a graphical element that is associated with a particular sensor may depend, for example, on the sensor's location (identified or inferred) in the image, and on the output value of the sensor at, or approximately at (e.g., shortly before or after) the time when an image is taken. The location of a graphical element with respect to a displayed image, the radius (R) of the graphical element, its size, color, shape, and/or orientation are example display attributes of graphical elements. (Other display attributes may be used.)

Acquiring a radioscopic image of a bodily organ and reading the sensors' output may preferably be performed simultaneously or concurrently, or within a permitted (e.g., sufficiently narrow) time window, in order to facilitate spatiotemporal synchronization between display of the image of the organ and display of the representation symbol. In the context of the present disclosure, 'spatiotemporal synchronization' refers to a temporal condition where an image of an organ is acquired and the sensor output values reflecting its physiological parameter(s) (e.g., any combination of temperature, pressure, acidity, etc.) are concurrently read, measured, or otherwise detected, and to a spatial condition where each sensor's output value is symbolically visualized (e.g., by using the pertinent graphical element) on the image or under the image at a location coinciding with, or otherwise corresponding or in relation to, the location of the sensor in the image. A graphical element may be visually superimposed with (e.g., overlaid on or underlaid under) a displayed image at the identified (or inferred) location of the pertinent sensor in that image. If a graphical element is visually underlaid under a displayed image at an identified (or inferred) location of the pertinent sensor in that image, the image may be made fully or partly transparent in the coincident area(s) or in the corresponding area(s) in order to make the underlying ('deeper') graphical element visible. The way a graphical element is displayed on top of, or underneath, an image (e.g., an image of an organ, or an image including an image of an organ) (e.g., the element size, color, etc.) may depend on the value(s) of the display attribute(s) which, in turn, may depend on the value of the pertinent sensor's output that is measured at the time when the image of the organ is acquired, or shortly before that time or thereafter.

Graphical elements may be constructed individually, as separate graphical objects that make up a displayable representation symbol, or collectively, as one graphical object. A displayable representation symbol may be a graph connecting data points that respectively represent the output values of the sensors. Data points, graphical objects or graph segments related to or representing the sensors may be located at a distance (spaced away) from a 'baseline' that represents, or connects, the locations of the sensors in an image. The distance of each data point, graphical element/object or graph segment from the baseline may indicate, be dependent on or derived from the output value of the pertinent sensor. Optionally, each distance may be biased with respect to the baseline; that is, a line representing zero value of the related measured parameter (e.g., pressure), against which the distances of the data points/graphical objects/graph segments may be determined (e.g., calculated), may be displaced a fixed distance from the baseline, for example, to avoid obscuring or shadowing the image at the location of the imaged bodily organ and/or sensors, and hence the imaged/studied bodily organ. Two or more sets of sensors may be used to detect different parameters, and as many displayable representation symbols may be visually superimposed with a same image.

A radioscopic image display method may include positioning one or more sets of sensors (one or more sensing elements) in, on, along, or adjacent to one or more bodily organs, where each sensors set may sense a different physiological parameter of an organ, acquiring a radioscopic image of the organ and simultaneously or concurrently reading the output values of the sensors; constructing one or more displayable representation symbols, a displayable representation symbol per sensing element, that respectively represent the sets of sensors and their output values, and visually (and in the case of two or more representation symbols, simultaneously) superimposing the (displayable) representation symbol(s) with the radioscopic image such that each (displayable) representation symbol is spatially synchronized to the location of the pertinent sensors, and temporally synchronized with respect to the output values of these sensors. 'Acquiring a radioscopic image' refers to the process where a bodily organ is exposed to high-energy electromagnetic radiation, and a matrix of radiation detectors outputs an electrical signal representative of the radiation sensed by the radiation detectors.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures:

FIGS. 3A-3B show tables according to an example embodiment;

FIGS. 9A-9B depict an example radioscopic image of an organ and physiological data symbolically displayed on top of it according to yet another example embodiment;

DETAILED DESCRIPTION

Figure 1A:
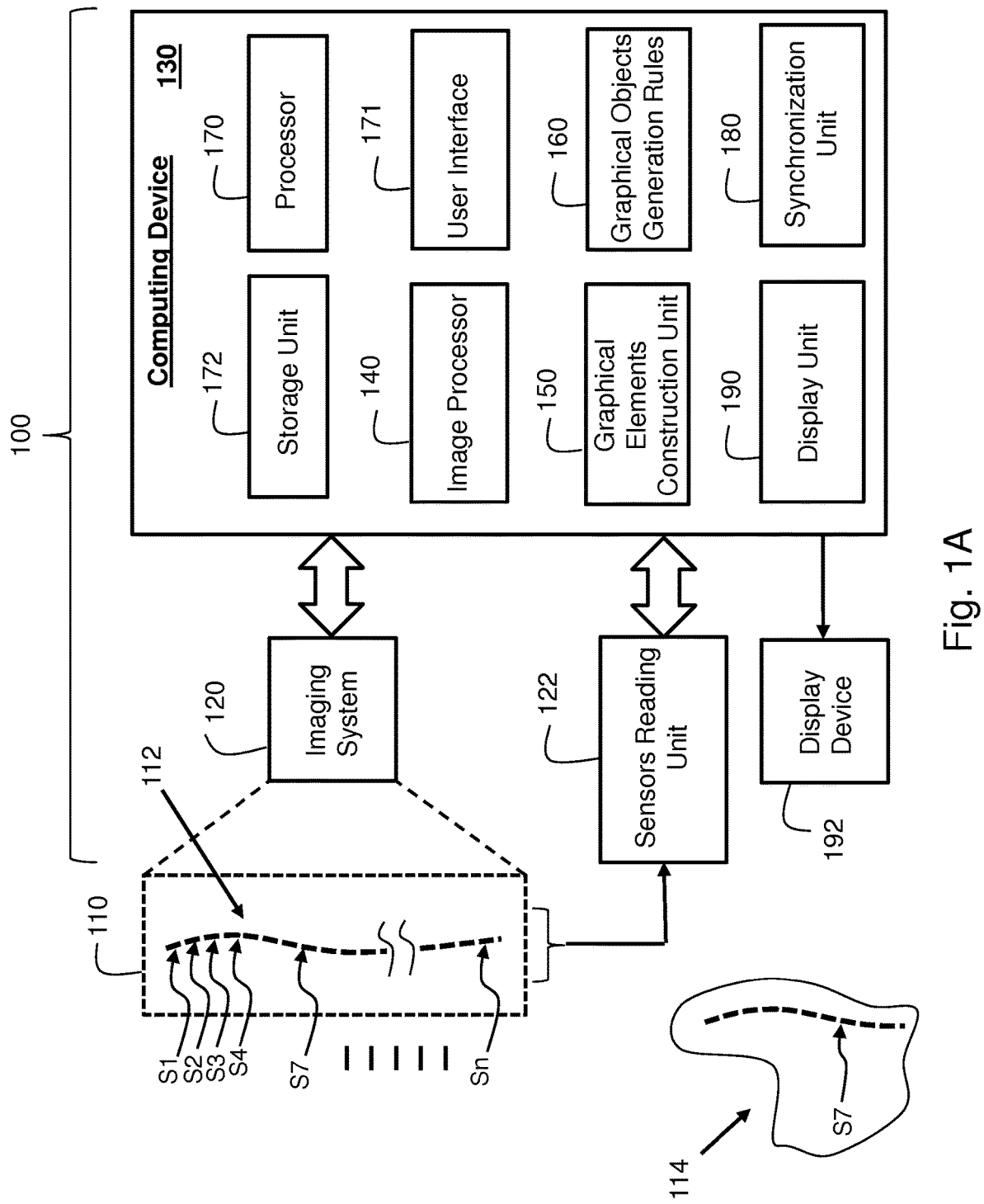
FIG. 1A is a block diagram of a visualization system according to an example embodiment.

The description that follows provides various details of exemplary embodiments. However, this description is not intended to limit the scope of the claims but instead to explain various principles of the invention and the manner of practicing it.

Although embodiments of the invention are not limited in this regard, discussions utilizing terms such as, for example, "processing," "computing," "calculating," "determining," "inferring", "deducing", "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information non-transitory storage medium that may store instructions to perform operations and/or processes. Unless explicitly stated, the method embodiments described herein are not constrained to a particular order or sequence of steps, operations or procedures. Additionally, some of the described method embodiments or elements thereof can occur or be performed at effectively the same point in time.

A variety of medical imaging technologies have been developed, which are capable of producing images of the interior of the human body, for example for diagnostic purposes. Radiography is frequently used for this purpose, and fluoroscopy, is one radiography technology that provides for real time imaging of bodily organs/structures in motion. Radioscopic (e.g., fluoroscopic) images are produced by measuring the intensity of radiation passing through a region of interest ("ROI") of the patient. Since sensed, or detected, radiation intensity varies as a function of the radio opacity (radiopacity) of the organs within the imaged region, the sensed or detected intensity represents the anatomical organ or structure within the ROI. In radioscopic imaging, the intensity of the detected radiation is represented as a visible image. An image frame may be created for each such radioscopic image, which frame may contain image data and metadata. Successive image frames may be used to create a video clip that enables visualizing the organ/structure in the ROI in motion. The video clip may be produced from successive radioscopic images and displayed in real time (e.g., while the organ is being imaged), or it may be recorded and played back on a monitor later (post hoc) for analysis. In some procedures, radioscopic imaging is used in real time to aid in the positioning of medical tools, stents, etc. in bodily lumens. The medical tool, stent, etc. may be built with radio discernible markers (e.g., radio opaque markers) that may absorb or scatter most of the used radiation such that when imaged, the markers are visibly conspicuous relative to the background. The radio discernible markers may be placed at strategic positions in the tools or stents, such as at their distal end, to enable a radiologist/technician to easily determine the location and/or orientation of the device.

It is also known that a contrast material may be introduced into the patient to delineate organs or structures, as part of a radiology study, by using radioscopic imaging. The contrast material may reveal functioning of blood vessels, the genitourinary system, or the gastrointestinal (GI) tract (e.g., esophagus, small bowel, colon, etc.), to name a few. Known contrast materials include barium, in the form of barium sulfate (BaSO4), which may be administered orally or rectally, for example for GI tract evaluation, and iodine in various proprietary forms. Contrast materials absorb or scatter a significant amount of x-ray radiation and may be used with real time radiographic/fluoroscopic imaging to visualize various dynamic bodily processes (by using still images or motion effect).

One such dynamic bodily process that is more and more studied using radiographic imaging with contrast materials is the esophageal peristalsis. Esophageal peristalsis involves contraction of circular muscles in the esophagus, in a wave-like form, to propel food and drink through the esophagus to the stomach. Normally, a contraction wave begins at the upper end of the esophagus and propagates downwardly toward the lower esophageal sphincter ("LES"). Some medical disorders (e.g., achalasia, dysphagia, diffuse esophageal spasm, ineffective esophageal motility, and hypertensive LES) are characterized by having abnormal contraction pattern of the esophagus. Radiographic imaging with contrast materials may also be used for detecting and characterizing oropharyngeal dysphagia, which arises from abnormalities of muscles, nerves or structures of the oral cavity, pharynx, and upper esophageal sphincter. The radiographic diagnostic procedure used to characterize oropharyngeal dysphagia is known as a modified barium swallow study ("MBSS").

The imaging techniques described above may be used to identify the location of a series or set of radio discernible sensors in a radioscopic image relative to one another and relative to the imaged bodily lumen, organ or structure. Once a location of a particular sensor is identified (or inferred) in a radioscopic image, a graphical element representative of the sensor location and its output value may be constructed and visually superimposed with the radioscopic image (whether by being overlaid on or underlaid under the image) of the bodily lumen, organ or structure, at the location of the particular sensor, or at a location corresponding to the sensor location.

The present invention is advantageous with respect to prior art systems/methods because visually superimposing physiological data with a video, as disclosed herein (e.g., in an spatiotemporally synchronized way), may provide significant enhancements to diagnostic utility of either modality alone or together, because of the intuitively recognizable relationship between organ structural function (as seen in video) and the underlying physiology (as seen in the displayed data).

FIG. 1A is a block diagram of a visualization system 100 according to an embodiment of the invention. Visualization system 100 may include an imaging system 120 for obtaining radioscopic images of a region of interest (ROI) 110 in a patient's body, a sensors reading unit ("SRU") 122 for reading or measuring, or otherwise detecting sensor output values, a computing device 130 for receiving image data (and possibly other data) from imaging system 120 and sensors' information (e.g., identification information, output values) from SRU 122, and for processing the image data and the sensors information, and a display device 190 for displaying radioscopic images and representation symbols representative of the sensors' output values.

Before the radioscopic imaging/study is commenced, a sensing element 112 may be inserted into the bodily organ whose physiological functionality is to be studied. Sensing element 112 may include n sensors, designated as S1, S2, . . . , Sn. Sensors S1, S2, . . . , Sn may be inserted into the ROI by using, for example, a catheter, or by using any other suitable method. The physical spacing between sensors S1, S2 . . . , Sn may be known a priori and used to identify the sensors in radioscopic images. One or more sensors may be designed slightly differently than others in order for them to serve as fiducial indicia in radioscopic images, in order to facilitate identification of the first sensor, second sensor, etc. in each radioscopic image. Special radio discernible markers may be built into the sensing device, or a radiographic 'signature' of certain non-sensing components of the sensing device may be used, to facilitate identification of the ordered sensors from images.

Any commercially available medical imaging system may be used for imaging ROI 110. Radio discernible sensors 112 may have any suitable size, shape, and material composition that may render them detectable by computing device 130 from the image produced by Imaging System 120. Imaging system 120 may image the ROI prior to the introduction of a contrast material to establish a baseline image. Once a suitable contrast material is introduced into ROI 110, imaging system 120 may be configured to acquire a series of images.

Computing device 130 may be of a type known in the art for processing medical image data, and it may interoperate with imaging system 120 to receive the series of radioscopic images in real time or in non-real time. Computing device 130 may be configured to perform steps of the display methods disclosed herein by using computer-executable modules or instruction codes that may be stored, for example, in a storage unit 172, and executed by a suitable processor (e.g., processor 170). Computing device 130 may also include an image processor 140, a graphical elements construction unit ("GECU") 150, graphical object generation rules 160, a synchronization unit 180, and a user interface 171 to enable a user to manipulate displayable representation symbols. Image processor 140 may process radioscopic image data that it receives from imaging system 120, for example, to identify the body lumen or organ, and sensors S1, S2, ..., S8 (or some of them) in each radioscopic image.

Sensor Outputs Reading, and Association of Output Values with Imaged Sensors

Sensors reading unit (SRU) 122 may be configured to read or measure, or otherwise detect, the output values of sensors S1, S2, ..., Sn. Serially or in parallel Since detection of sensor outputs is faster than the imaging process, the output of the sensors may be detected, for any image, in series, one sensor output after another. SRU 122 may transfer the sensor output readings (values) to computing device 130, and computing device 130, by using, for example, image processor 140 or processor 170, may respectively associate the n sensors' output values with the n sensors after image processor 140 identifies the sensors in the related image. If image processor 140 cannot, or does not, identify a sensor in an image, it may infer its location in the image from identified locations of other sensors and/or from sensors identified in previous or subsequent images when multiple images are processed, such as in a video stream, and computing device 130 may handle 'inferred' sensor locations as if they were identified; i.e., in the same way as it handles identified sensors. It is not necessary to always identify all the identifiable sensors: the requirement or preference to identify all or particular sensors may change from one application to another.

By using the information transferred from SRU 122 (e.g., sensors' identification codes, sensors' output values, etc.), computing device 130 may 'know' which sensor that computing device 130 identifies in the image is the first sensor (e.g., topmost in the image, or leftmost in in the image, etc.), the second sensor, and so on, and which measured output value is associated with (read/measured from) which sensor. SRU 122 may be a separate apparatus or a component thereof or embedded in computing device 130.

Inferring Location of Unidentified Sensors

As explained herein, one or more sensors of sensing element 112 may not be identifiable in a radioscopic image, for example due to it/them being radioscopically indiscernible. If image processor 140 cannot identify a particular sensor (e.g., sensor S7, as illustrated at 114), image processor 140 may infer the location of the sensor (e.g., sensor S7) using any suitable method, for example, use of knowledge of the sensing device construction (e.g., sensor spacing); interpolating/extrapolating the sensor location from prior and/or subsequent image frames in which currently indiscernible sensors are discernible; performing velocity estimation (which may be beneficial in cases where sensors are blurred or smeared due to motion) using a host of techniques including, for example, estimation from blurred shape, frame-to-frame delta position analysis, etc. Other methods may be used to infer the location of an unidentified sensor.

In order to infer a location of a sensor in an image, image processor 140 may use two or more known (identified) sensor locations to calculate a straight line or a curved line that passes via the (e.g., connects) these locations. Based on a priori information related to sensing element 112, such as the number and size of the sensors and the spacing between them, image processor 140 may calculate the location(s)/coordinates of the unidentified sensors. (The calculated location(s) may be point(s) lying on or adjacent the calculated line.)

Synchronization

Synchronization unit 180 may synchronize between imaging system 120 and SRU 122 in order to enable image processor 140 to timely associate the correct sensors' output values to the sensors that are identified in an image (and also to inferred sensors, if applicable). That is, if an image of bodily organ(s) is acquired/pictured at time T1, it is beneficial to know the sensors' output values corresponding to the organ(s) at the same time T1, as this may enable computing device 130 to display the image (e.g., using display device 192) with a symbolic representation of the relevant sensors' output values on top of (e.g., superimposed or overlaid on) the image, rather than displaying a symbolic representation of output values from a different (non-synchronized) time on that image. Computing device 130 may alternatively display the image with a symbolic representation, or representation symbol, of the relevant sensors' output values underlaid under the image, in which case computing device 130 may make the image transparent in the area above or overlapping the sensors' output values, in order to make the sensors' output values visible. An image or a representation symbol need not be evenly transparent. That is, different areas in the image, or in the representation symbol, may have different levels of transparency. The different transparency levels may be determined, for example, so that a user viewing the image and the representation symbol, or representation symbols, can see all the graphical elements of the representation symbol(s) through the image, or the entire image through all the graphical elements of all the representation symbols.

Synchronization unit 180 may initiate an image and data co-display cycle during which imaging system 120 may acquire an image of the ROI and SRU 122 may synchronously/timely detect the sensors' outputs at the image acquiring time. During the image and data co-display cycle, image processor 140 may receive (e.g., from imaging system 120) a signal representative of an image frame, process the image data to delineate (or otherwise accentuate or emphasize) the bodily organ(s) and the sensors it can identify (and, if required, inferentially determine, and thereafter delineate, the location of unidentified sensors), and display unit 190 may display (e.g., on display device 192) the bodily organ(s) and, in addition, a displayable symbolic representation of the sensors' output values on top of the bodily organ(s), in a spatiotemporally synchronized manner. (The shorter the image and data co-display cycles, the better, because radioscopic images can be acquired and displayed—with up to date sensor values overlaid on, or underlaid under, them—at higher rates.)

A subsequent image and data co-display cycle may commence at any time between the initiation time and end time of a current image and data co-display cycle, and image and data co-display cycles may slightly differ in time length due to changes that may occur, for example, in the number of sensors that are identified in an image. For example, the greater the number of unidentified sensors in an image, the lengthier the process that handles these sensors. Synchronization unit 180 may monitor or keep track of the progress of each image and data co-display cycle in order for it to be able to determine when a subsequent image and data co-display cycle can be commenced. Synchronization unit 180 may monitor the progress of each image and data co-display cycle by, for example, receiving information from image processor 140, and/or from processor 170, that pertains, for example, to the image capturing and processing, and to the construction of the displayable symbolic representation of the sensors' output values.

Generating a Displayable Representation Symbol for the Sensors

GECU 150 may generate a displayable symbolic representation for symbolically visualizing the set of sensors' output values in the way described below, for example in connection with FIGS. 2A-2E and FIGS. 3A-3B. (Other displayable symbolic representations, or representation symbols, for symbolically visualizing a set of sensors' output values may be used.) Display unit 190 may display the displayable symbolic representation, or a representation symbol, on display device 192 such that the displayable symbolic representation and the related image are visually superimposed. That is, the displayable symbolic representation may be visually overlaid on a related image of the bodily organ(s), or it may be visually underlaid under the image. (By 'related image' is meant an image acquired at, or approximately at, the time at which the sensors' output values were sampled/scanned/detected). Display unit 190 may alternatively display the image with the relevant symbolic representation, or representation symbol, underneath the image, in which case display unit 190 may make the image transparent in the coincident areas (the image areas above or overlapping the graphical elements representing the sensors' output values) in order to make the symbolic representation, or representation symbol, visible.

GECU 150 may use one or more rules of graphical objects generation rules 160 to generate the displayable symbolic representation, or representation symbol, of the sensor's outputs. Graphical objects generation rules 160 may include a set of rules that may be used to generate the displayable symbolic representation of the sensor's outputs. Some rules may depend on the type of the used representation symbol. Other rules may define ways to make the representation symbol visually conspicuous despite intensity changes that radioscopic images may undergo. For example, one rule may be used to determine the size of a graphical element of the displayable symbolic representation, or representation symbol; another rule may assign a color to the graphical element such that the graphical element is made visually conspicuous, etc.

A displayable symbolic representation, or representation symbol, may be constructed as one graphical object that may represent the location and output of all the sensors, or as a collection of graphical elements where each graphical element may represent a particular one of the sensors. Representation of a sensor means locating the pertinent graphical object, or an element thereof associated with the sensor, at the identified location of the sensor, or at a location corresponding to the sensor's identified location, and displaying the graphical object, or the element thereof, using one or more display attributes whose value(s) are indicative of the sensor's output value.

Latency Between Video Stream and Sensors Data Stream

Typically, there is a delay between the actual occurrence of a physiological event (e.g., muscle contraction, temperature change, acidity change, etc.) and the transfer of image data and/or sensor data to computing device 100, and also a delay that may be due, for example, to the different data processing time that is involved in processing each type of data (image data, sensor data) by the data acquisition equipment (e.g., imaging system 120, sensor reading unit 122, etc.). An additional delay may be due to, for example, different data transfer rate of the image data and sensor data. If such delays are sufficiently different to result in a significant loss of time synchronization between the data sets, they need to be compensated for. This may be done by measuring and/or estimating each of them and applying a time correction offset to the respective data sets so that the data presented in the combined visualization (of the image and representation symbol) represents the state of the studied organ at the same (or nearly so) instant in time. The measuring and/or estimating of the time delays may be done off-line if these delays are stable, or dynamically if they change in time.

Since synchronization between displaying of images and displaying of sensor data is, therefore, to be maintained throughout the imaging procedure, the difference in latency between the two data streams, or data sets, may be compensated for, for example by computing device 100 using a synchronization unit identical or similar to the one shown in FIG. 1B, which is described below.

Figure 1B:
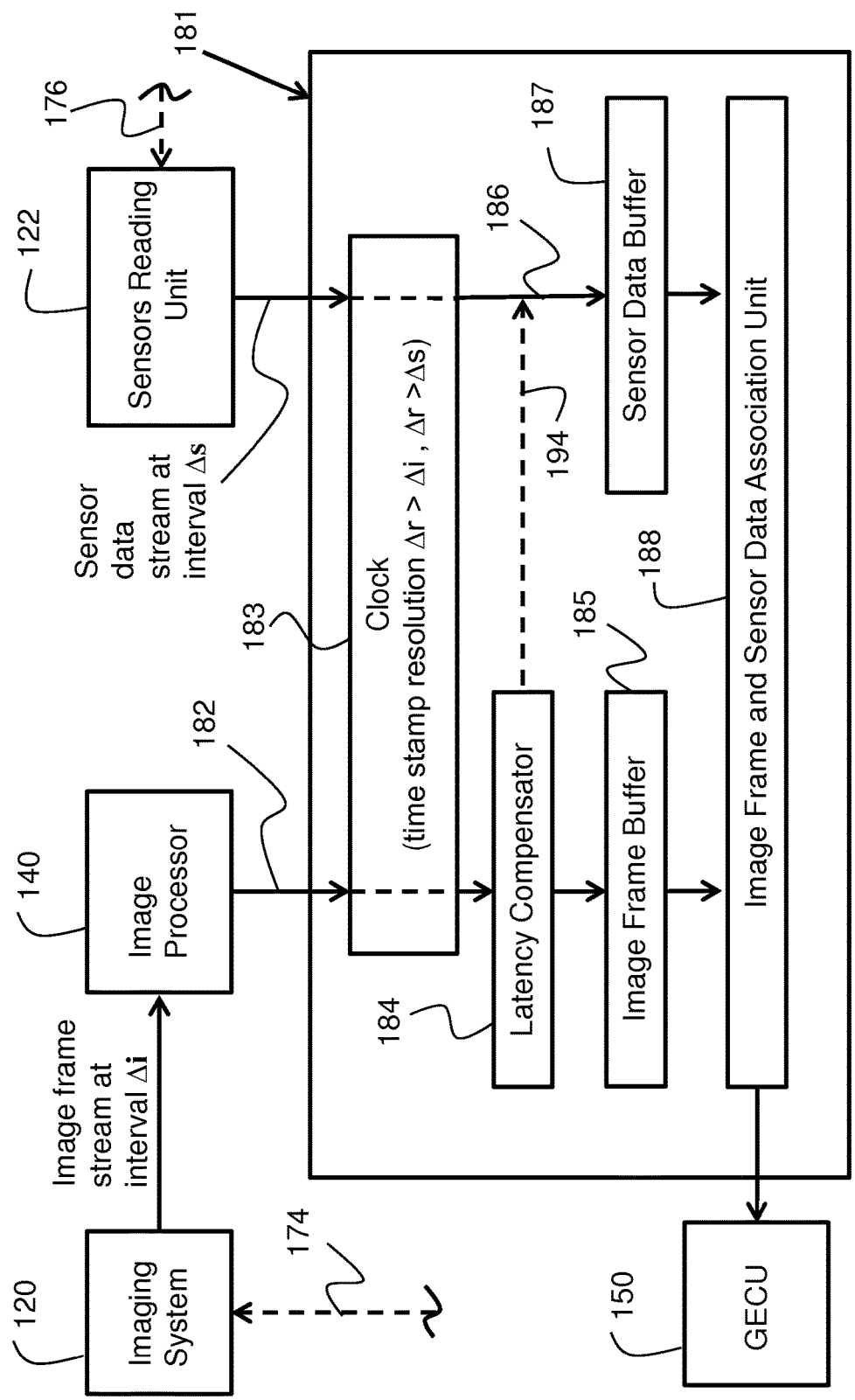
FIG. 1B is a block diagram of a synchronization unit according to an example embodiment.

FIG. 1B shows a block diagram of a synchronization unit 181 according to an example embodiment of the invention. (Synchronization unit 181 may function in the same way as synchronization unit 180 of FIG. 1A, or in a similar way.) Imaging system 120 may acquire radioscopic images and transfer, to image processor 140, corresponding image frames at interval Δi. Image processor 140 may transfer the image data (or a processed version thereof), and also sensor location data related to identified and/or inferred sensor locations, to latency compensator 184. (The image data, or the processed version thereof, and the sensor location data that are transferred to latency compensator 184 are shown at 182.) Clock 183 may time stamp image frames, for example on-the-fly, before they reach latency compensator 184. Each time-stamped image frame may be buffered in image frame buffer 185. While image frames are continued to be generated by imaging system 122, sensor reading unit 122 may read the output values of the sensors at interval Δs, and forward (186) a sensor data stream to sensor data buffer 187 after clock 183 time stamps sensor data 'chunks', for example on the fly. (A 'sensor data chunk' is data that includes sensors' output values measured, sampled, or read for the same image frame.)

Latency compensator 184 may narrow temporal gaps between image frames and sensor data chunks, or equalize the latencies involved, in the way described below. Latency compensator 184 may offset (e.g., delay) each time-stamped image frame using a fixed amount of time. Latency compensator 184 may alternatively offset (e.g., delay) time-stamped image frames using a variable/changeable delay, setting an offset value per image frame, or per a group of successive image frames. Latency compensator 184 may determine the offset value for each image frame, or once in a while (e.g., every nth image frame; e.g., every 5th image frame), by calculating, on the fly, time differences between timestamps of image data and timestamps of sensor data chunks. Latency compensator 184 may monitor (194) timestamps of the sensor data stream in order to be able to calculate the timestamp differences. Latency compensator 184 may use the time calculation results to dynamically adjust the offset value in order to, for example, accommodate for latency changes.

Image frame and sensor data association ("IFSD") unit 188 may associate each image frame in image frame buffer 185 with corresponding sensor data chunk in sensor data buffer 187. IFSD unit 188 may associate between an image frame and a sensor data chunk by comparing the image frame's timestamp to the timestamps of the sensor data chunks that are stored in sensor data buffer 187, and selecting the sensor data chunk whose timestamp is the closest to the timestamp of the image frame as the sensor data chunk that is to be associated with that image frame. (The association process may be repeated for each image frame.) Every time IFSD unit 188 finds (in sensor data buffer 187) a sensor data chunk for an image frame, IFSD unit 188 may forward, for example, the sensor data associated with the image frame and the sensor location data (and possibly the image frame) to graphical elements construction unit (GECU) 150. GECU 150 may use the sensor data and sensor location data (and possibly, the image frame) to construct a displayable representation symbol that represents the sensor data. Imaging system 120 may be controlled (174), e.g., by a synchronization unit (e.g., by synchronization unit 181, synchronization unit 180), or by processor 170. Sensor reading unit 122 may be controlled (176), e.g., by a synchronization unit (e.g., by synchronization unit 181, synchronization unit 180), or by processor 170.

Figure 2A:
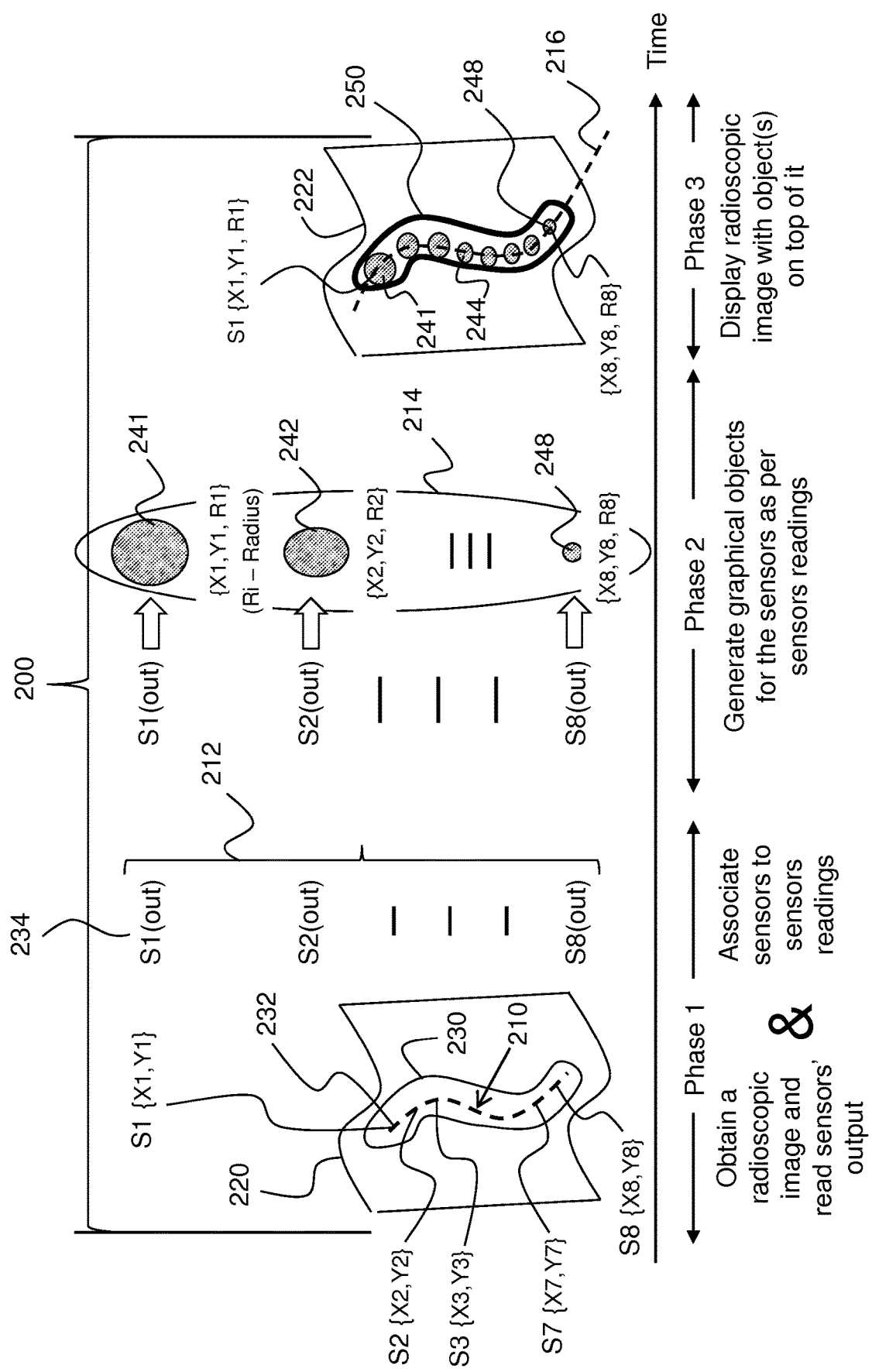
FIGS. 2A-2D schematically illustrate image and data co-display cycles according to some example embodiments.

FIG. 2A schematically illustrates a co-display cycle 200 according to an embodiment of the invention. Assume that eight sensors (n=8), designated as S1, S2, ..., S8, are positioned in a bodily organ, for example by using a catheter (the catheter is not shown in FIG. 2A). Assume that the studied bodily organ is the pharynx and adjacent structures, and sensors S1 to S8 are pressure sensors disposed to measure the pressures associated with swallowing. (Sensors similar to sensors S1-S8 may likewise be disposed in other bodily organs; e.g., in the esophagus, small bowel, or colon, and they may be of the same type; e.g., pressure sensors, or of various types; e.g., pressure sensors and temperature sensors, pressure sensors and acidity sensors, etc.) An image and data co-display cycle may be divided into three phases, as described below. Sensors S1, S2, ..., S8, by being disposed along, or in, the imaged bodily organ (in this example in the esophagus), for example by using a catheter or other means, may lie on a line 210 whose curvature may match the curvature of the bodily organ being studied.

Phase 1 of the Image and Data Co-Display Cycle

During the first phase (phase 1), ROI 220 (with esophagus 230 in it) may be radioscopically imaged, for example by imaging system 120, with sensors S1 to S8 disposed in esophagus 230, and the output values of sensors S1-S8 may concurrently or synchronously be read, for example by SRU 122 (the sensors' outputs are 'conceptually' shown at 212).

Image processor 140 may identify all or some of the sensors S1-S8 in the radioscopic image. (In the example of FIG. 2A it is assumed that all of the sensors are identified by image processor 140.) After image processor 140 identifies the sensors, it may determine the relative location of each sensor by using any suitable coordinates system. For example, using the Cartesian coordinates system, it may determine that sensor S1 is positioned at point {X1,Y1} (as shown at 232), sensor S2 is positioned at point {X2,Y2}, sensor S3 is positioned at point {X3,Y3}, and so on.

Image processor 140 may respectively associate the output values of sensors S1-S8 with these sensors. For example, the sensor output value associated with (i.e., read from) sensor S1 is sensor value S1(out) (as shown at 234), the sensor output value associated with sensor S2 is sensor value S2(out), the sensor output value associated with sensor S3 is sensor value S3(out), and so on.

Phase 2 of the Image and Data Co-Display Cycle

During the next phase (phase 2), a displayable representation symbol 214 may be generated, for example by GECU 150, for the output values 212 of sensors S1-S8. Displayable representation symbol 214 may be generated as a single displayable graphical object that may include, in this example, eight graphical elements (a graphical element per sensor). In the example shown in FIG. 2A the displayable elements are filled circles. Each displayable element, in this example it is a filled circle, may represent a particular one of the eight sensors S1-S8. By "a displayable element representing a particular sensor" is meant that display attributes or particulars of the displayable element may depend on, or stem or derived from, the location of the particular sensor in the image, and on/from the output value of that sensor at the image acquiring time, or shortly before or after that time. Display attributes/particulars of a displayable element may include, for example, the location/position of the displayable element relative to the location/position of other displayable elements, color, size, shape, length, radius, etc.

The location/position of the displayable element, or a predetermined point thereof, may be determined based on the location (e.g., coordinates) of the pertinent sensor as identified in the image. For example, the location/position of the displayable element, or the predetermined point thereof, may overlap or coincide with the location of the pertinent sensor as identified in the image. Other display attributes/particulars of the displayable element (e.g., color, radius, etc.) may be determined based on, or they may be derived from or depend on the output value of the sensor for which the displayable element is constructed.

For convenience of illustration, the displayable filled circles, an example of graphical elements, of displayable representation symbol 214 are shown in phase 2 respectively depending on the sensors' output values but disassociated from the sensors' locations in the image. For example, display attributes/particulars {X1,Y1,R1} may be associated with filled circle 241 that may be associated with (it may be constructed for) sensor S1, where {X1,Y1} designate the location of sensor S1 (or its inferred location) in the image, and {R1} designates the radius of the circle whose value depends on the value of sensor S1 at the image acquiring time, or shortly before or after that time. Likewise, display attributes/particulars {X2,Y2,R2} may be associated with filled circle 242 that may be associated with (it may be constructed for) sensor S2, where {X2,Y2} designate the location of sensor S2 in the image, and {R2} designates the radius of the circle whose value depends on the value of sensor S2 at the image acquiring time, or shortly before or after that time, and so on. Additional displayable elements may be constructed in a similar way for some other sensors or for all sensors. Alternatively, filled circles 241, 242, ..., 248 of displayable symbolic representation 214 may be generated individually/separately, as multiple graphical objects (e.g., one graphical object per sensor's location and output value), using display attributes/particulars that may be identical or similar to the attributes/ particulars described herein, for example above (e.g., in connection with the various elements of displayable object 214).

Phase 3 of the Image and Data Co-Display Cycle

During the next phase (phase 3), the imaged ROI may be displayed, for example by display unit 190, for example on display device 192, with the eight filled circles 241-248 displayed on top of it. In the displayed image 222 are shown the imaged bodily organ 250 (in this example the organ is the pharynx and proximal esophagus, and it is shown delineated) and the eight filled circles 241-248. As explained herein, displayable representation symbol 214 may be constructed and displayed on top of bodily organ 250 as a single object, in which case each of filled circles 241-248 may be an element within that object, or as a single multi-object representation, in which case filled circles 241-248 are constructed and displayed in image 222 individually. Filled circles 241-248 are shown in displayed image 222 respectively positioned according to the locations $\{X1,Y1\},\{X2,Y2\},\ldots,\{X8,Y8\}$ of sensors S1-S8 as identified from the image, and respectively sized according to the output values S1(out), S2(out), ..., S8(out) of sensors S1-S8.

Assuming that sensor S2 has the greatest output value when the ROI is imaged (e.g., $S2(out)>S1(out)\geq S3(out)\geq,\ldots,\geq S8(out)$), it may be determined that the radius R2 of filled circle 242 (which is the filled circle generated for sensor S2) may be, for example, greater than the radius of the other filled circles (e.g., $R2>R1\geq R3\geq,\ldots,\geq R8$). Since the positions of circles 241-248 in image 222 respectively correspond to or stem from the identified (and inferred) locations of sensors S1-S8 in the image (and, therefore, to the location of sensors S1-S8 in the ROI), circles 241-248 may be aligned with or arranged according to a baseline 216 whose shape/curvature may resemble the shape/curvature, for example, of the catheter carrying the sensors. (Baseline 216 may be visible or invisible in image 222). That is, baseline 216 may have a shape/curvature resembling the shape/curvature of line 210. Circles 241-248 may be positioned and sized on baseline 216 as per their display attributes/particulars. Since sensors S1-S8 reside in organ 230, line 210, along which the sensors are positioned, may closely simulate the natural anatomical curvature of imaged organ 230. When organ 230 moves (e.g., spontaneously), for example from one image to another, as may happen when a video clip generated from successive images of ROI 220 is played, whether in real time or not, so does line 210 and, therefore/consequently, line 216.

Image Video

Each image and data co-display cycle may start by radioscopically acquiring an image of a ROI (e.g., by imaging system 120) and simultaneously reading or measuring the output values of the n sensors (n=1, 2, 3, ...,) (e.g., by SRU 122) that may sense one or more physiological parameters (e.g., pressure, or pressure and impedance, etc.) of an organ residing in the imaged ROI. An image and data co-display cycle may be regarded as terminated when the imaged ROI is displayed (e.g., using display device 192) with a symbolic representation, which is associated with the locations and values of the sensors, on top of, or underlying the image of the ROI. Synchronization unit 180 may operate imaging system 120 to acquire a stream of images of the ROI, and SRU 122 to read/measure the sensors' output. A stream of images may facilitate generation of a video clip that may visualize process dynamics of, or related to, the imaged/studied bodily organ. For example, due to anatomically-induced changes (e.g., movement of a peristaltic wave, temperature changes, etc.) that some or all of the sensors may experience as the imaging study progresses over time (e.g., from one image to another, or from one set of images to another), some sensors, and consequently their displayable representations, may visually appear to be moving in the imaged ROI, and/or their display attributes or particulars (e.g., color, size, radius, length, curvature, etc.) may change, thus visualizing, in intuitive way, the behavior pattern or dynamics of the imaged organ.

Figure 2B:
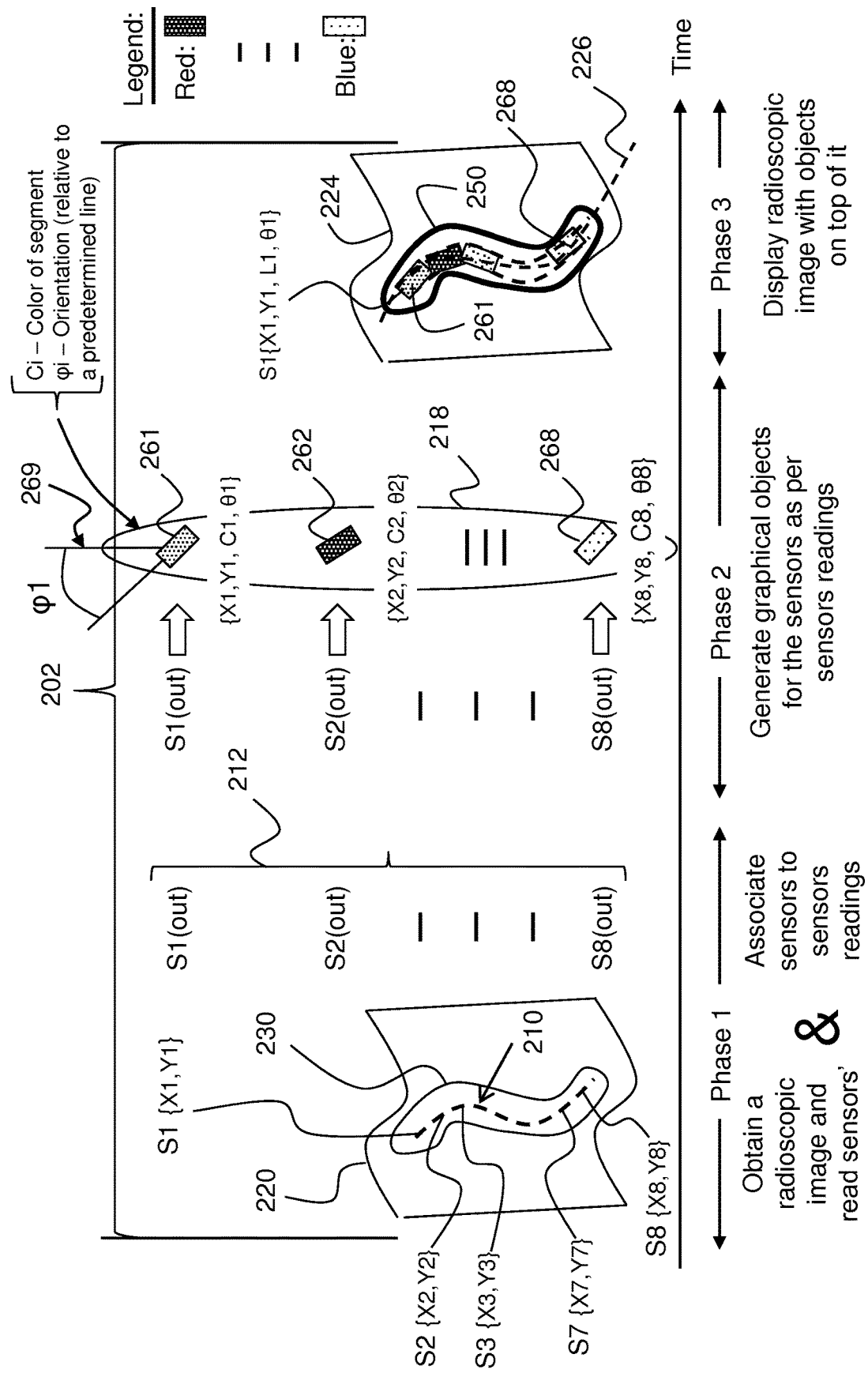

FIG. 2B schematically illustrates an image and data co-display cycle 202 according to another embodiment of the invention. Assume that the example phase 1, phase 2 and phase 3 of FIG. 2A are applicable also to FIG. 2B, but the two drawings differ in the displayable symbol used to represent the sensors; e.g., the difference being the way the sensors' output values are visualized in image 224.

Phase 2 of the Image and Data Co-Display Cycle

During phase 2, a displayable representation symbol 218 may be generated, for example by GECU 150, for output values 212 of sensors S1-S8. Displayable representation symbol 218 may be generated as a single displayable graphical object (e.g., as a color bar or color ribbon) that may include, in this example, eight displayable elements (a displayable element per sensor). In the example shown in FIG. 2B the displayable elements are colored rectangles, and each colored rectangle may be associated with (e.g., constructed for) one particular sensor. The colored rectangles may be visually seamlessly connected to one another. The colors of the rectangles may respectively depend on the sensors' output values. By way of example, the greater the value of an output value of a sensor, the redder the color of the rectangle associated with (i.e., constructed for) the sensor. (The colors are represented in FIG. 2B by black dots of varying density; e.g., the denser the dots in a rectangle, the redder the rectangle.) Each colored rectangle may represent (be associated with, or constructed for) a particular one of the eight sensors S1-S8, with the representation meaning being explained herein. The location/position of the color rectangle, or a predetermined point thereof, may be determined based on the location (e.g., coordinates) of the pertinent sensor as identified in the image. For example, the location/position of the color rectangle, or the predetermined point thereof, may overlap or coincide with the location of the pertinent sensor as identified in the image.

For conveniency, the displayable rectangles of displayable object 218 are shown in phase 2 respectively depending on the sensors' output values but disassociated from the sensors' locations in the image. For example, display attributes/particulars $\{X1, Y1, C1, \varphi1\}$ may be associated with color rectangle 261 that may be associated with (generated for) sensor S1, where $\{X1,Y1\}$ designate the location of sensor S1 (or its inferred location) in the image, $\{C1\}$ designates the rectangle's color corresponding to the value of sensor S1 at the image acquiring time, or shortly before or after that time, and $\{\varphi1\}$ designates the tilt angle of rectangle 261 with respect or relative to a predetermined line, for example with respect or relative to a reference line 269. The tilt angle may reflect the angle, or the derivative of a curvature, of the catheter inside the imaged bodily organ at the point/location of the sensor for which the related color rectangle is constructed. By using this parameter, the color rectangles may be constructed such that they would lie on a line whose shape may resemble the shape of the catheter, and aligned with that line.

Likewise, display attributes/particulars $\{X2, Y2, C2, \varphi2\}$ may be associated with colored rectangle 262 that may be associated with (it may be constructed for) sensor S2, where $\{X2,Y2\}$ designate the location of sensor S2 in the image, {C2} designates the rectangle's color corresponding to the value of sensor S2 at the image acquiring time, or shortly before or after that time, and {φ2} designates the tilt angle of colored rectangle 262 with respect the reference line.

Additional displayable elements may be generated in the same way for some other sensors or for all the sensors. Alternatively, colored rectangles 261, 262, . . . , 268 of displayable representation symbol 218 may be generated individually, as multiple graphical objects (e.g., one graphical object per sensor's output value), using display attributes/particulars that may be identical or similar to the attributes/particulars described herein, for example above (e.g., in connection with the various elements of displayable representation symbol 218).

Phase 3 of the Image and Data Co-Display Cycle

During the next phase (phase 3), an image 224 of imaged ROI 220 may be displayed, for example by display unit 190, for example on display device 192, with the colored rectangles 261-268 visually superimposed on it. (As discussed herein, visually superimposing two objects (e.g., radioscopic image and a representation symbol or symbolic representation) may mean visually overlaying a first object on a second object, or visually underlying the first object under the second object, as the case may be.)

In image 224 are shown an image 250 of bodily organ 230 and colored rectangles 261-268 that are respectively positioned in agreement, or in unison, with the location of sensors S1 to S8, and respectively colored according to the sensor output values, as described herein. As explained herein, displayable representation symbol 218 may be constructed and displayed, in a spatiotemporally synchronized way, on top of image 224 or image 250 of the bodily organ as a single object, in which case each one of colored rectangles 261-268 may be an element that may be spatiotemporally synchronously displayed atop a location corresponding to the related sensor. (Representation symbol 218 may, alternatively, be underlaid under image 224 or image 250, with the image 224 (or image 250) being transparent to make representation symbol 218 visible.) Alternatively, displayable representation symbol 218 may be constructed and displayed as a multi-object representation, in which case colored rectangles 261-268 may each be constructed and displayed in image 224 individually, such that each colored rectangle is visually overlaid on or underlaid under, in a spatiotemporally synchronized way, the pertinent sensor.

Colored rectangles 261-268 are shown in image 224 respectively positioned according to the locations {X1,Y1}, {X2,Y2}, . . . , {X8,Y8} of sensors S1-S8 as identified (and inferred) in the image, respectively colored according to the output values S1(out), S2(out), . . . , S8(out) of sensors S1-S8, and aligned with line 226. Assuming that sensor S2 has the greatest output value when ROI 220 is imaged (e.g., S2(out)>S1(out)≥S3(out)≥, . . . , ≥S8(out)), it may be determined that the color of rectangle 262 (which is the rectangle generated for sensor S2) may be, for example, the reddest (as illustrated by the rectangle 262 containing the most dense dots among rectangles 261-268). Colored rectangles 261-268 may be constructed as one color bar or color ribbon, or as contiguous color rectangles that visually appear (for example in image 224) as a color bar or color ribbon.

Since the position (coordinates) and tilt of colored rectangles 261-268 in image 224 correspond to or stem from the identified (and inferred) locations of sensors S1-S8 in the image of the ROI, rectangles 261-268 may be aligned with or arranged according to a baseline 226 whose shape may resemble the shape, for example, of the catheter carrying the sensors. (Baseline 226 may be visible or invisible in image 224). Rectangles 261-268 may be positioned on, and aligned with, baseline 280 as per their display attributes/particulars. Since sensors S1-S8 reside in organ 230, line 210, along which the sensors may be positioned, may closely represent the natural anatomical shape/curvature of organ 230. When organ 230 moves (e.g., spontaneously), for example from one image to another, as may happen when a video clip generated from successive images of ROI 220 is played, whether in real time or not, so does line 210 and, therefore, line 226.

Figure 2C:
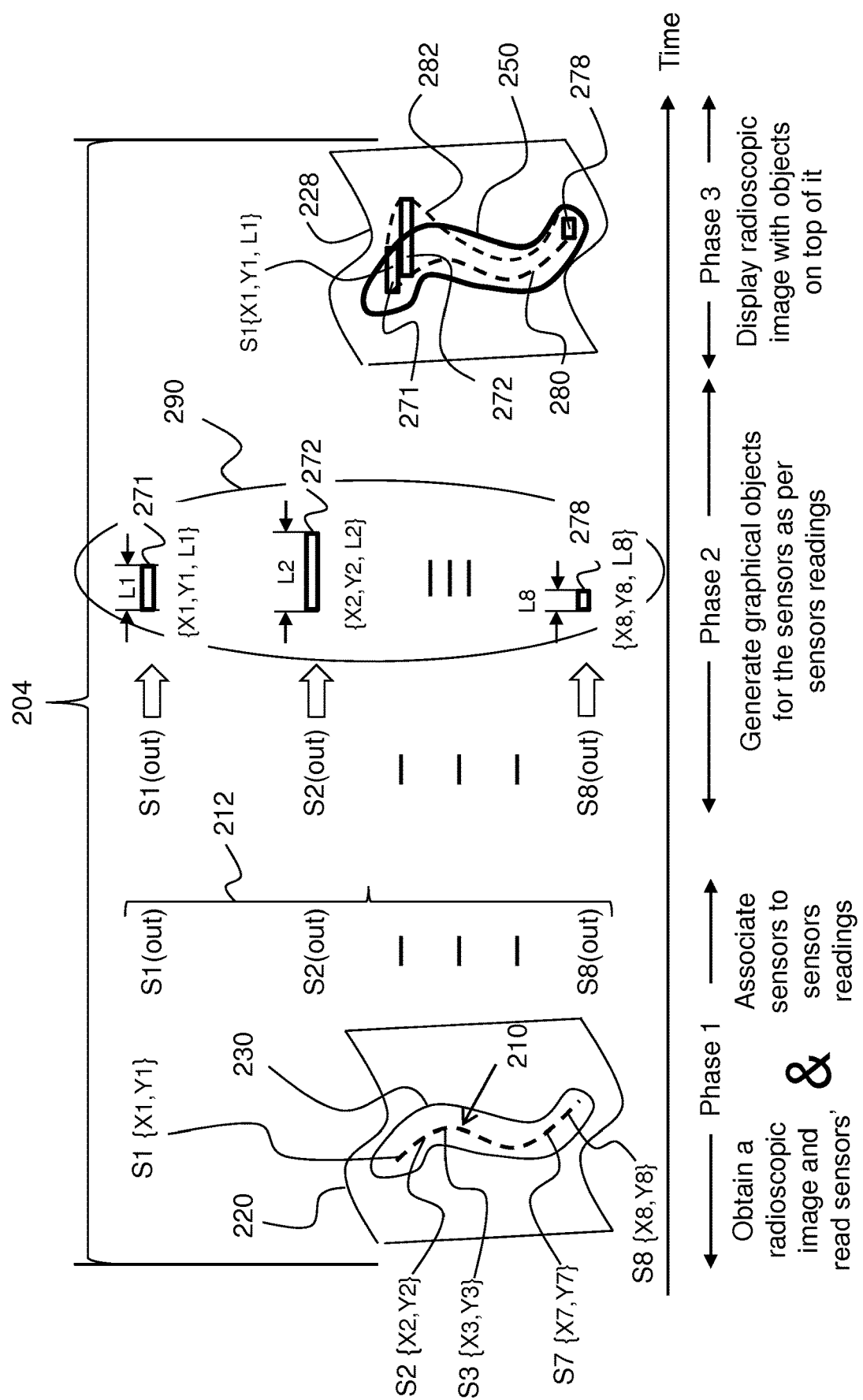

FIG. 2C schematically illustrates an image and data co-display cycle 204 according to yet another embodiment of the invention. Assume that the example phase 1, phase 2 and phase 3 of FIGS. 2A-2B are applicable also to FIG. 2C, but FIG. 2C differs in the displayable symbol that represents the sensors; i.e., in the way the sensors' output values are visualized in image 228.

Phase 2 of the Image and Data Co-Display Cycle

During phase 2, a displayable representation symbol 290 may be generated, for example by GECU 150, for the output values 212 of sensors S1-S8. Displayable representation symbol 290 may be constructed as a single displayable graphical object that may include elements/segments that, in this example, are 'bars', where each bar may be associated with (e.g., constructed for) one particular sensor. The length (Li, i=1, 2, 3, . . . ) of each bar may depend on, or be a function of, the output value of sensor Si. For example, the greater the value of an output value of sensor Si (i=1, 2, . . . , ), the greater the length, Li, of the bar associated with sensor Si. The location/position of each bar, or a predetermined point thereof, in image 228 may be determined based on the location (e.g., coordinates) of the pertinent sensor as identified in the image. For example, the location of a bar, or the predetermined point thereof, may overlap or coincide with the location of the pertinent sensor as identified in the image. By having locations that respectively depend on the locations of the (identified) sensors, and lengths that respectively depend on (to represent) the output values of the sensors, each bar may represent a particular one of sensors S1-S8. For conveniency, the bars of displayable representation symbol 290 are shown in phase 2 respectively depending on the sensors' output values but disassociated from the sensors' locations in the image.

By way of example, display attributes/particulars {X1, Y1,L1} may be associated with bar 271 that is associated with (constructed for) sensor S1, where {X1,Y1} designate the location of sensor S1 (or its inferred location) in the image, and {L1} designates the bar's length corresponding to the output value of sensor S1 at the image acquiring time, or shortly before or after that time. Likewise, display attributes/particulars {X2,Y2,L2} may be associated with bar 272 that is associated with (constructed for) sensor S2, where {X2,Y2} designate the location of sensor S2 (or its inferred location) in the image, and {L2} designates the bar's length corresponding to the output value of sensor S2 at the image acquiring time, or shortly before or after that time, and so on.

Additional displayable elements (in this example these element are bars) may likewise be generated for some other sensors or for all the other sensors. Alternatively, bars 271, 272, . . . , 278 of displayable representation symbol 290 may be constructed individually, as multiple graphical objects (e.g., one graphical object per sensor), using display attributes/particulars that may be identical or similar to the attributes/particulars described herein, for example above (e.g., in connection with the various elements of displayable representation symbol 290).

Phase 3 of the Image and Data Co-Display Cycle

During the next phase (phase 3), the image of the ROI may be displayed, for example by display unit 190, for example on display device 192, with the bars 271-278 displayed on top of it, or under it. In image 228 are shown image 250 of the bodily organ and bars 271-278. As explained herein, displayable representation symbol 290 may be constructed and displayed on top of, or under, bodily organ 250 as a single object, in which case each one of bars 271-278 may be an element within that object, or as a multi-object representation, in which case bars 271-278 may be constructed and displayed in image 226 individually. Bars 271-278 are shown in image 228 respectively positioned according to the locations {X1,Y1},{X2,Y2}, . . . , {X8,Y8} of sensors S1-S8 as identified in the image, and respectively having lengths according to the output values S1(out), S2(out), . . . , S8(out) of sensors S1-S8.

Assuming that sensor S2 has the greatest output value when the ROI is imaged (e.g., S2(out)>S1(out)≥S3 (out)≥, . . . , ≥S8(out)), it may be determined that bar 272 (which is the bar constructed for, or the bar representing, sensor S2) may be longer than the other bars. Sensors having lower output values may be represented by shorter bars, with their lengths respectively depending on the output values of the sensors.

Since the locations of bars 271-278 in image 228 correspond to or stem from the identified (and inferred) locations of sensors S1-S8 in the image of the ROI, bars 271-278 may be aligned with or arranged on or in relation to a baseline 280 that may coincide with the identified (and inferred) locations of the sensors and resemble the shape, for example, of the catheter carrying the sensors (e.g., it may resemble line 210). (Baseline 280 may be visible or invisible). Bars 271-278 may extend from baseline 280 as per their lengths. Since sensors S1-S8 reside in organ 230, line 210, along which the sensors may be positioned, may closely represent the natural anatomical shape/curvature of imaged organ 230. When organ 230 moves (e.g., spontaneously), for example from one image to another, as may happen when a video clip generated from successive images of ROI 220 is played, whether in real time or post hoc/factum, so does line 210 and, therefore, line 280. A line 282 may be constructed such that it connects the distal (extended) ends of bars 271-278 (the proximal ends of the bars assumed to lie on line 280.) Line 282 may be displayed in addition to bars 271-278 or instead of them.

Figure 2E:
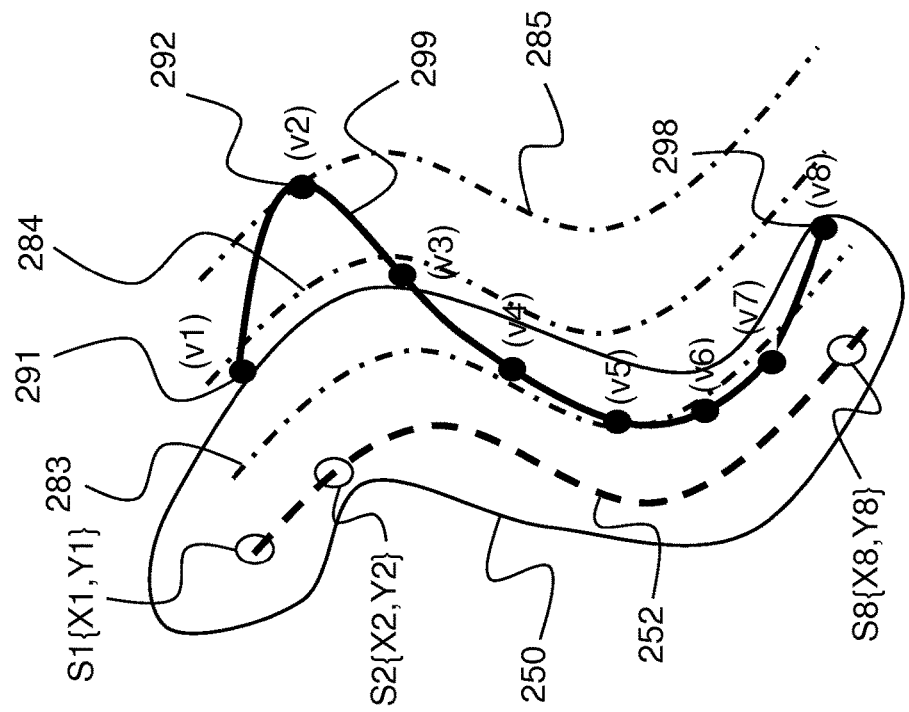
FIGS. 2E-2F schematically illustrate display of imaged organs according to another example embodiments.
Figure 2D:
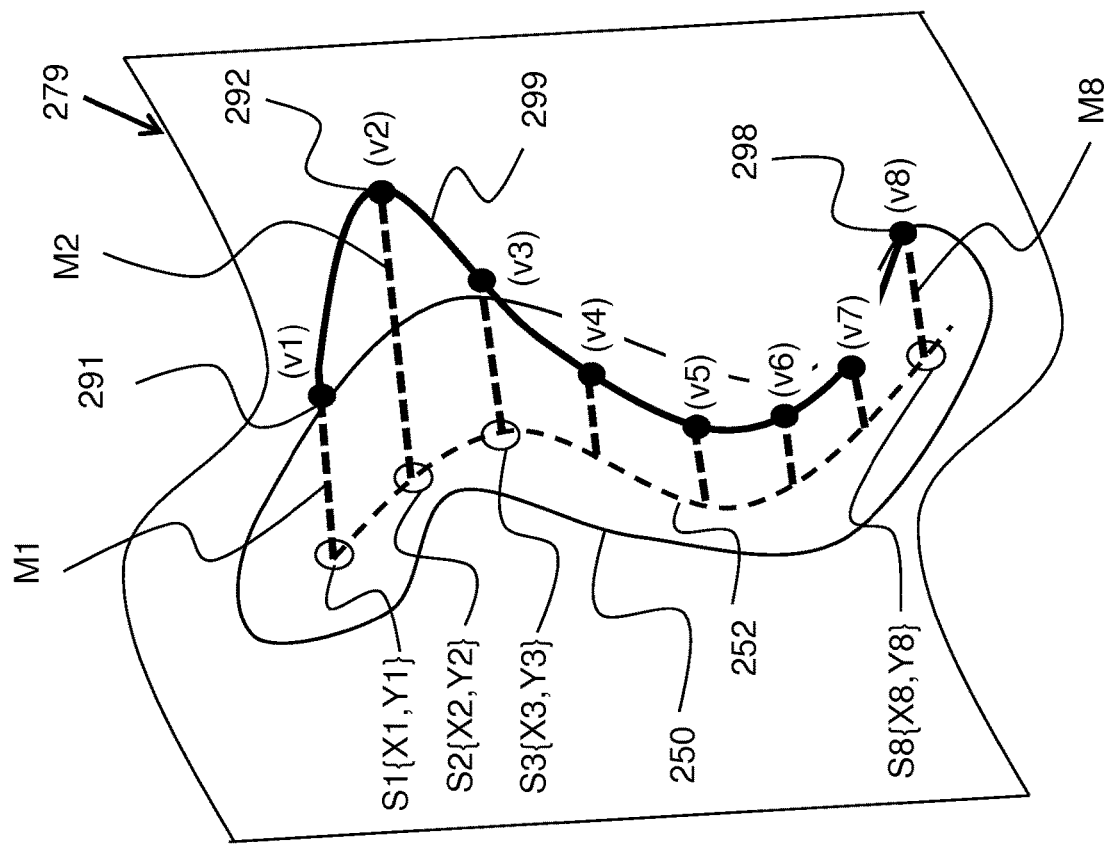

FIG. 2D schematically illustrates a displayable image 279 according to another embodiment of the invention. Assume that phase 1, phase 2 and phase 3 of FIGS. 2A-2C are applicable to FIG. 2D, except for the way the sensors' output values are representatively displayed on top of the image of the bodily organ. Image 279, which may be displayed during a third phase of an image and data co-display cycle, may contain an image of a studied bodily organ (the organ's image is shown at 250), a baseline 252 that may pass via or adjacent the identified (and inferred) locations S1{X1,Y1}, S2{X2,Y2}, . . . , S8{X8,Y8} of sensors S1, S2, . . . , S8, respectively, and a graph 299 that may visualize the output values v1, v2, v3, . . . , v8 of sensors S1 to S8 (v1, v2, . . . , v8 may respectively represent or correspond to S1(out), S2(out), . . . , S8(out)). For example, data point 291 may represent output value v1, or S1(out), of sensor S1, data point 292 may represent output value v2, or S2(out), of sensor S2, and so on. Data point 291 may be obtained by calculating a vector (M1) whose origin may coincide with, or substantially coincide with (e.g., it may be adjacent), the identified (or inferred) location of sensor S1 as defined by coordinates {X1,Y1}, and whose magnitude, or length, M1, may be equal to, or derived from, the output value v1 of sensor S1; data point 292 may be obtained by calculating a vector whose origin may coincide with, or substantially coincide with (e.g., it may be adjacent), the identified (or inferred) location of sensor S2 as defined by coordinates {X2,Y2}, and whose magnitude, or length, M2, may be equal to, or derived from, the output value v2 of sensor S2, and so on. All of vectors M1, M2, . . . , M8 may be orthogonal to baseline 252 but they need not, as demonstrated by FIG. 2D that shows them as parallel lines. Graph 299 may be calculated and constructed, for example as a single graphical object, during phase 2 of the image and data co-display cycle, as per, or based on, the {X,Y} coordinates of data points 291, 292, . . . , 298. (The dots on graph 299 are shown only for illustration purpose; they need not be displayed. Vectors M1, M2, . . . , M8 may be visible or invisible)

FIG. 2E illustrates FIG. 2D with contour lines according to an example embodiment of the invention. FIG. 2E depicts the same baseline 252 and graph 299 of FIG. 2D, and, in addition, three example isolines, which are designated as 283, 284 and 285. Each of isolines 283, 284 and 285 may represent a line of equal or constant value of a physiological parameter, as per the type of the used sensors. For example, if sensors S1 to S8 measure, for example, pressure, then each of isolines 283, 284 and 285 may be a line of equal or constant pressure. (For example, isolines 283, 284 and 285 may respectively designate 0 mmHg, 50 mmHg, and 100 mmHg.) If, according to another example, sensors S1 to S8 measure temperature, then each of isolines 283, 284 and 285 may be a line of equal or constant temperature. (For example, isolines 283, 284 and 285 may respectively designate 30 degrees Celsius, 35 degrees Celsius, and 40 degrees Celsius. Using isolines such as isolines 283, 284 and 285 facilitates easy and intuitive interpretation of graph 299. For example, since, by way of example, graph 299 intersects isoline 285 at point 292, point 292 designates the value of isoline 285, be it a pressure value, temperature value, impedance value, Electromyography value, or any other parameter.

Figure 2F:
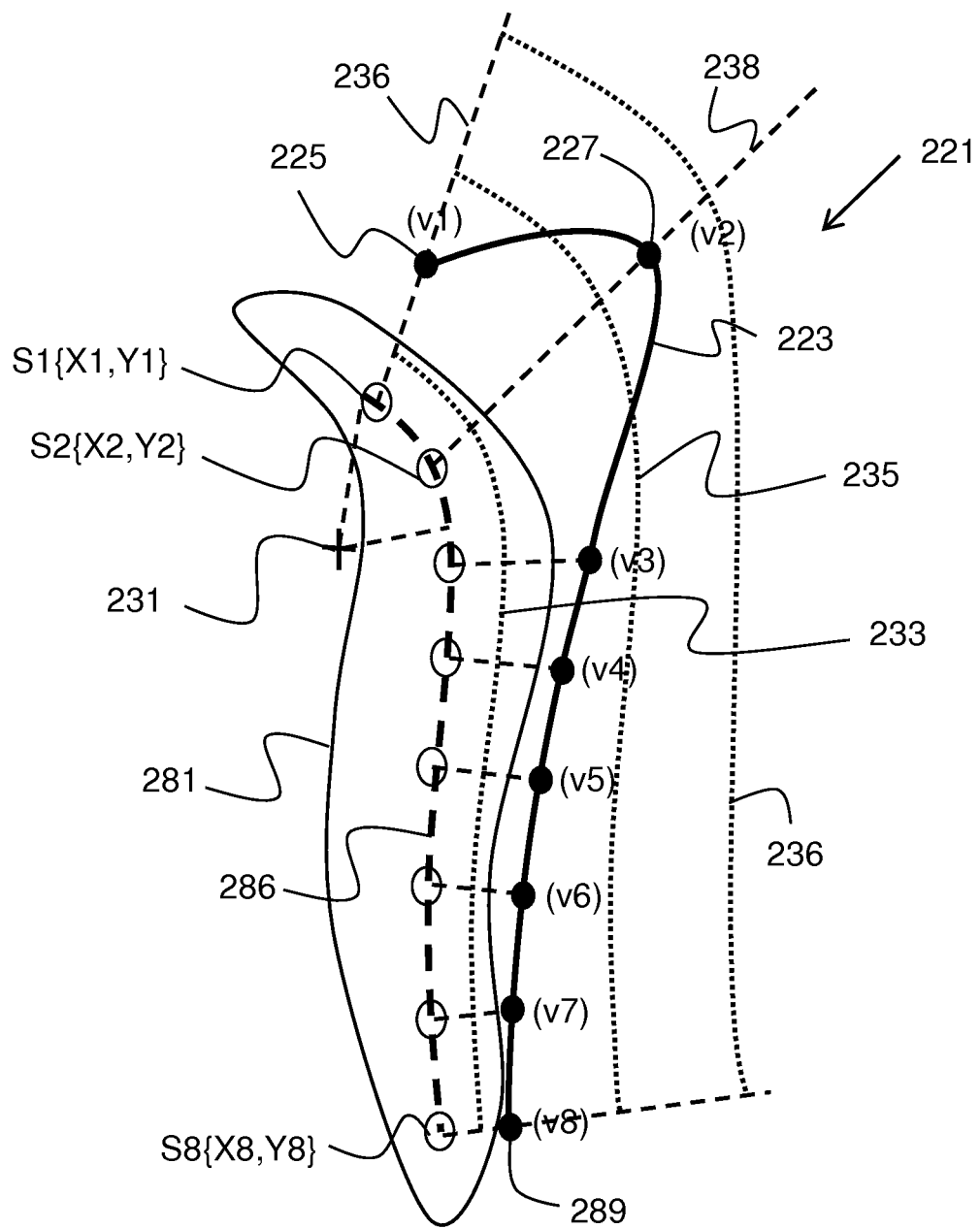

FIG. 2F schematically illustrates a radioscopic image 221 and a graph 223 according to another example embodiment of the invention. By way of example, image 221 includes an image 281 of a bodily organ (e.g., pharynx), a baseline 286 that represents the locations of eight sensors S1-S8 (other numbers of sensors may be used; e.g., fewer sensors; e.g., 4 sensors, or more than eight sensors; e.g., 12 sensors). The location of example sensors S1, S2, . . . , S8 in image 221 are S1{X1,Y1}, S2{X2,Y1}, . . . , S8{X8,Y8}, respectively, and the output values of sensors S1, S2, . . . , S8 are v1, v2, . . . , v8, respectively. Baseline 286 has a conspicuous, or main, curvature, the center of which is shown at 231. The rest of baseline 286 is generally a straight line. For display convenience, graph 223 may be constructed on the convex side of baseline 286, which is the side of baseline 286 that 'bulges' outwardly (in this example baseline 286 bulges to the right). (The convex side of baseline 286 is the baseline side opposite the side of curvature center 231.)

A data point 225 representing the output value v1 of sensor S1 may reside on a line 236 perpendicularly extending from baseline 286 at location S1{X1,Y1}), at a distance (from the sensor's location S1{X1,Y1}) corresponding to or representing the output value v1 of sensor S1. A data point 227 representing the output value v2 of sensor S2 may reside on a line 238 perpendicularly extending from baseline 286 at location S2{X2,Y2}), at a distance (from the sensor's location S2{X2,Y2}) corresponding to or representing the output value v2 of sensor S1. Data points corresponding to the other sensors values (e.g., v3, v4, and so on) may be found in a similar way, and graph 223 may be constructed such that it passes through the data points 225, 227, etc., and through interpolated or extrapolated data points. (Graph 223 may be a smoothed line; that is, without the black circles shown on it.) Baseline 286 and/or the lines perpendicularly extending therefrom may be made (e.g., by a command input via a user interface) visible or invisible.

Contour lines such as contour lines 233, 235 and 236 may visually be overlaid on or underlaid under radioscopic image 221 as reference lines. Each contour line may designate a particular parameter value. While baseline 286 may represent zero value of the parameter measured by the sensors, contour line (or isoline) 233 may designate a higher value V233, contour line 235 may designate a value V235 that is higher than the value V233, and contour line 236 may designate a value V236 that is higher than the value V235 (that is, 0<V233<V235<V236). Using isolines such as isolines 233, 235 and 236 may make interpretation of graph 223 easier. (Other numbers of isolines may be used; e.g., fewer isolines; e.g., 2 isolines, or more than three isolines; e.g., 6 isolines).

FIG. 3A shows an example table 300 according to an example embodiment of the invention. Table 300 may contain two types of data: (1) data related to the sensors (e.g., sensors' serial number, locations in an image and output values, as shown, for example, at 310), and (2) data related to display attributes of displayable representations (e.g., as shown, for example, at 320). Table 300 contains example information. The display attributes may pertain, for example, to multiple displayable element/objects that may be realized individually as filled circles (or as objects that may have any geometrical shape), or to one displayable element/object that may be constructed from, or include, multiple filled circles (or graphical elements/objects having other geometrical shape), where each such circle may be constructed as an individual graphical element of the (single) displayable object. For example, in the table entry holding data related to sensor number 1, the location of that sensor may be, for example, {89,224}, and the sensor's output value (measured, for example, in volt) may be, for example, 9.4 v. Therefore, the display attributes of the filled circle (be it an individual object or an element of a greater object) representing sensor number 1 may be the location {89,224}, which is the sensor's location (whether identified or inferred) in the related image, and the circle radius, R, may be equal to, for example, 4.95 millimeter. The radius R of a circle may be calculated by using, for example, formula (1):

$$R = R\max * (V/V\max) \quad (1)$$

where Rmax is the maximum radius a circle can have, V is the actual sensor's output voltage, and Vmax is the maximum voltage a sensor can output. For example, given that the sensor's maximum voltage, Vmax, is 10 v, and the maximum radius a circle can have is 5 mm, and the sensor's output value is 5 v, then the radius of the circle that represents that sensor's value may be 2.5 mm (R=5 mm*(5 v/10 v)=2.5 mm).

FIG. 3B shows an example table 330 according to another example embodiment of the invention. Table 330 may contain the same type of information as in table 300, as shown at 340 and 350, except that in table 330 the display attributes 350 may pertain to multiple displayable elements/objects that may be realized, for example, as color quadrilateral (e.g., colored bars, colored rectangles, colored trapezoids, etc.), or polygon in general, or to one displayable object that may be constructed from, or include, multiple color quadrilateral, where each such color quadrilateral may be an individual graphical element of the (single) displayable object. For example, in the entry related to sensor number 1, the display attributes of the related color bar (whether the bar is an individual object or an element of/in the greater object) representing sensor number 1 may be the location {89,224}, which is the sensor's location (whether identified or inferred) in the related image of the ROI, the color, C, of the bar may be, for example, red, and the orientation, or tilt φ, which may be calculated relative to some predetermined line, may be zero degrees. Table 330 contains example information.

Figure 4:
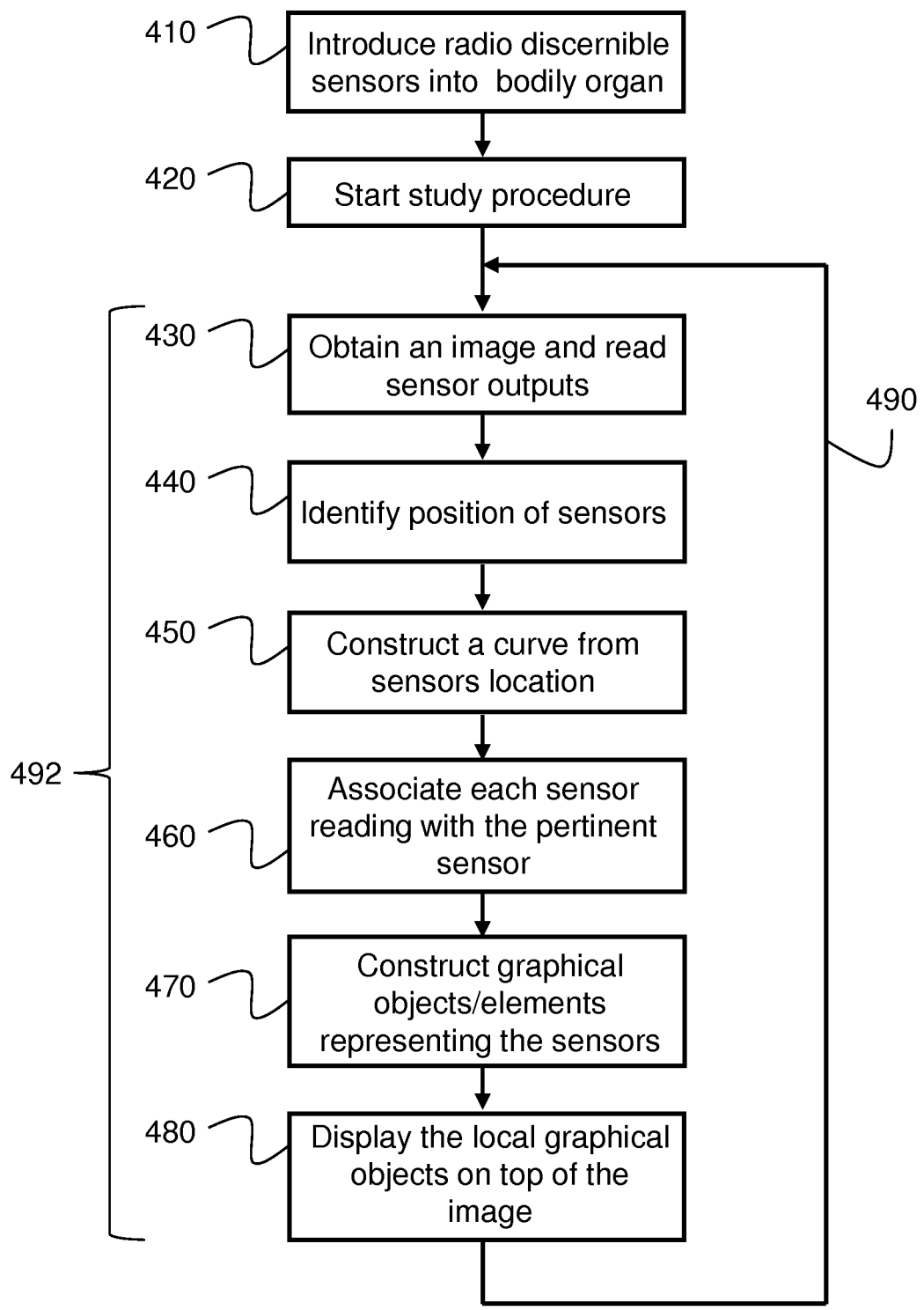
FIG. 4 is a bodily organ/structure visualization method according to an example embodiment.

FIG. 4 shows a bodily organ/structure visualization method according to an embodiment of the invention. At step 410, n sensors may be introduced into a bodily organ/structure in order to review/analyze the physiological dynamics of the bodily organ/structure, for example post hoc/factum. The sensors may be introduced into the organ by using, for example, a catheter, or they may be individually removably attached to locations of interest on, in, or near the organ. The sensors may be equidistantly spaced from one another, but they need not be. As described herein, two or more sets of sensors may be introduced into a bodily organ, with each set monitoring a different physiological parameter or aspect of the physiological dynamics of the bodily organ, or a different parameter or aspect of a physiological dynamics of a different bodily organ. For example, some sensors may be densely located in, or distributed along, a particular area or space of the organ, while other sensors may be sparsely located in, or distributed along, another area or space of the organ. The sensors, or some of them, may be radio discernible sensors, or they may include, or have associated with them, radio discernible markers. The location of a sensor in the radioscopic image may be found directly or straightforwardly if it is made of or include a radio discernible marker. If a sensor is not made of (nor does it include) a radio discernible marker, but rather have one or more reference radio discernible markers associated with it, then the location of the sensor in the radioscopic image may be determined indirectly, by using the reference radio discernible markers. For example, the location of the sensor may be determined inferentially, based on the location(s) of the one or more radio discernible markers in the image.

Once the sensors are set in place, a radioscopic study may be initiated, at step 420, to monitor the physiological dynamics of the imaged organ, or organs. The study may be conducted as known in the art, which may include initiating passage of a contrast material through the organ/lumen to be imaged. If, for example, the sensors are distributed within the pharynx or esophagus of a patient, a barium swallow study (MBSS) technique may be used. During the radiographic study, a series of radioscopic images may be taken, one image at a time (at step 430), for example, by using imaging system 120 or a similar system. The images may be taken sequentially in order to visualize, for example, movement of the contrast material in the studied organ. The imaging system may transfer image frames to a computing device (e.g., computing device 130) at a suitable fixed frame rate, or at irregular frame rate. Image frames may be time stamped to enable compensating for image data stream latency, as discussed herein, for example, in connection with FIG. 1B, and to facilitate construction of a video clip.

Figure 5:
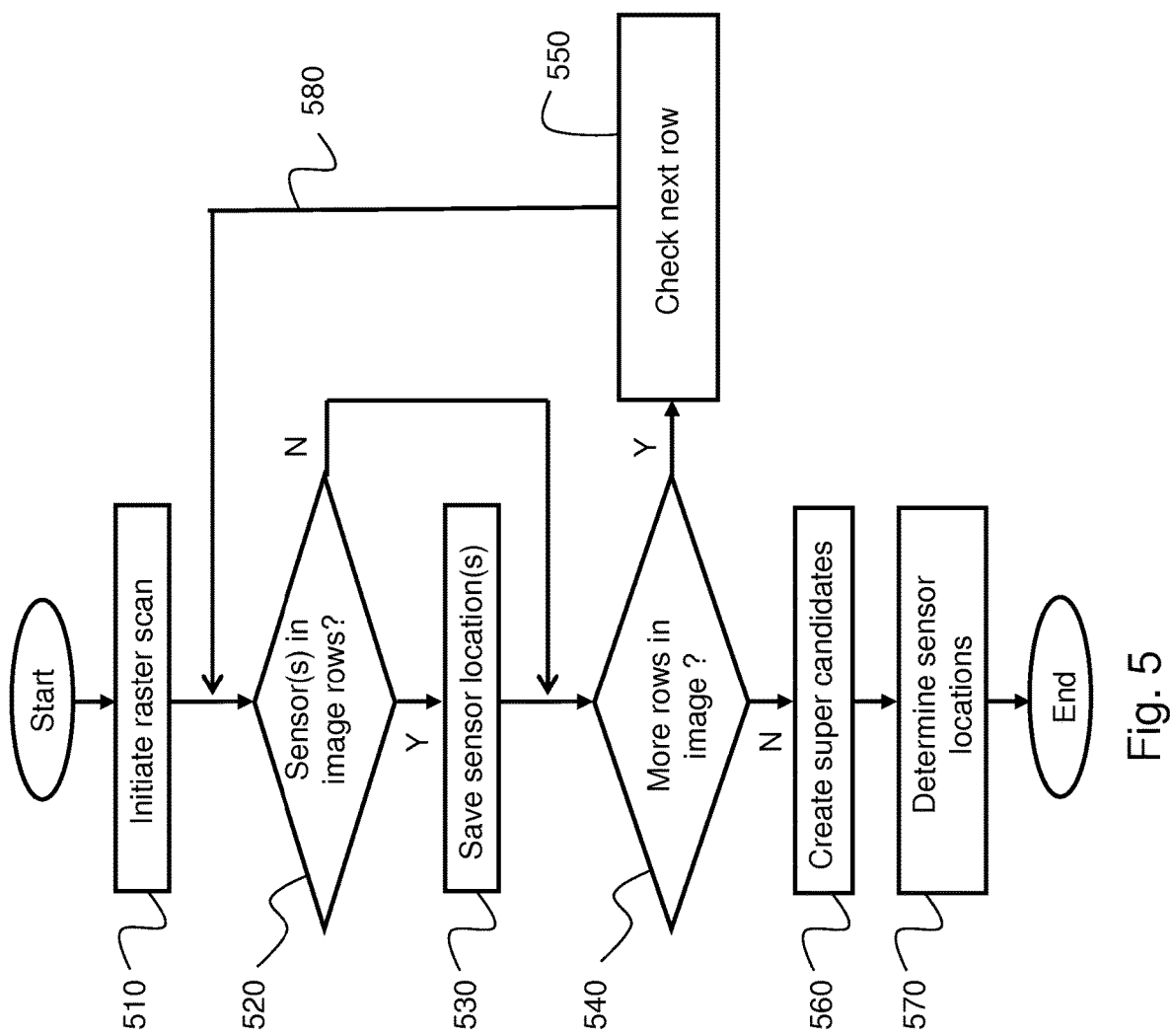
FIG. 5 is a method for identifying sensors in an image of a bodily organ/structure.

At step 430, an image and data co-display cycle may be initiated (e.g., by synchronization unit 180), and a radioscopic image of a ROI may be obtained, for example by imaging system 120 of FIG. 1. (As explained herein, the ROI may include the imaged organ, the sensors used to monitor its physiological dynamics, and background body organs/tissues.) At the time at which the image of the ROI is acquired, or shortly before or after that time, the sensor outputs may be read (e.g., by SRU 122), and each time a sensor's output is read, the sensor data representing the sensor's output value may be time stamped to enable compensating for image data stream latency, as discussed herein, for example, in connection with FIG. 1B, and to facilitate synchronization between sensors' values and the related image. At step 440, the position of the sensors in the radioscopic image may be identified (e.g., by image processor 140). Many possible routines may be used to identify the sensor locations, and any suitable routine may be used. For example, the sensor locations in radioscopic images may be identified by using raster scan, as shown in FIG. 5 that is described below.

At step 450, a curve, which is referred to herein as 'baseline', may be calculated or constructed from, or based on, the identified (and possibly on inferred) locations of the sensors. (The curve, or baseline, may be visible or invisible.) Any suitable curve calculating/constructing algorithm may be used to calculate/construct the curve/baseline. In FIG. 2A, for example, a curve 216 is constructed such that it may pass through sensor locations {X1,Y1}, {X2,Y2}, . . . , {X8,Y8}. In some embodiments, a polynomial curve fitting technique may be applied to an array of sensor positions (coordinates). Some curve forming algorithms may require that the sequence (e.g., order) of sensors be specified in order to ensure that the fitting algorithm correctly connects the (sequential) sensors. The appropriate sequence may be determined, for example, based on known sensor shape, size, and spacing (e.g., along a catheter). For example, a curve may be constructed from, or include, a series of lines connecting the locations of adjacent sensors in the sequence. In some situations, for example in situations in which the catheter is sharply bent, a more sophisticated curve forming algorithm may be required in order to cope with the relatively small radius bends of the catheter. The constructed curve may enable inferring (e.g., using interpolation or extrapolation) the position of unidentified sensors (e.g., unidentified due to them being radiographically obscured). The constructed curve may also serve as a baseline against, or in relation to, which a graph depicting, or visually representing, a physiological parameter (e.g., peristaltic pressure of the esophagus) may be constructed and displayed. The graph may be positioned, oriented and/or scaled in the radioscopic image such that it may be closely spatially aligned with or coincides with the catheter (for example), or positioned correctly in relation to the curve or line that represents the catheter.

At step 460, each sensor's output value may be associated with the pertinent sensor. At step 470, graphical objects/elements that may represent the sensors (and the sensors' output values) may be constructed, for example as described herein. At step 480, the graphical objects/elements representing the sensors may be displayed, in spatiotemporally synchronized way, overlaid on, or underlaid under, the radioscopic image the radioscopic image, as illustrated, for example, in FIGS. 2A-2F, and depicted in FIGS. 7, 8 and 9A-9B.

Execution of step 480 may terminate the image and data co-display cycle, and a subsequent image and data co-display cycle may commence in the same way using loop 490. That is, process 492 may be performed for each image in a series of radioscopic images. In some embodiments, these steps may be performed in real time. For example, the steps may be pipelined or performed before a subsequent image and data co-display cycle commences. Alternatively, some steps (e.g., steps 440-480 or steps 470-480) may be performed post hoc, at any suitable later time, for example to analyze the bodily organ dynamics after the diagnostic procedure ends. In some embodiments, radioscopic images may be processed during the study and may be processed again post hoc.

FIG. 5 is a method for identifying sensors in a radioscopic image of a bodily organ/structure. At step 510, a raster scan may be initialized and various parameters may be set. For example, the parameters may include the image to be scanned, minimum and maximum sensor diameter, brightness threshold(s), number of rows to be scanned simultaneously, and number of rows per increment. At step 520 a group of adjacent row(s) (e.g., initially a top group of rows) of the image may be scanned to identify candidate sensors. Candidate sensors may be identified by changes in image intensity along the scanned row or set of rows, which may be above a specified threshold, and the distance between intensity changes is not greater than the expected maximum diameter, width or length of the sensor. If sensors are identified in a group of adjacent rows, the sensor locations may be saved, at step 530. If there are more rows to scan (the condition being checked at step 540), the rows to be scanned are updated, at step 550, and the identification process of step 520 may be repeated, as per loop 580. Once all rows are scanned for candidate sensor locations (the condition being shown as "N" at step 540), "super candidate" sensor locations may be identified at step 560. A super candidate sensor location may be defined as a cluster of contiguous candidate locations in adjacent rows. The number of adjacent rows, in which a candidate sensor location may present before a sensor location is identified as a super candidate, may be determined in any suitable way. For example, the number of adjacent rows that may be scanned at any particular time may be specified by a user or determined from, or based on, the sensor sizes and image resolution. The timing at which super candidate locations may be identified may vary. For example, after each successive group of rows is scanned, the sensor locations in the group of rows may be analyzed with the sensor locations detected in previously scanned rows, to identify super candidate sensor locations.

The super candidate locations may then be further discriminated in step 570 by a variety of algorithmically implemented constraints including: being not more than the maximum sensor size, having the candidate sensor shape (and rotations thereof), having a known sensor spacing, and lying along a curve consistent with the minimum bend radius of the catheter to which the sensors may be attached and/or organ under study. Candidate sensor locations that are determined not to be part of a super candidate location may be ignored or discarded.

Step 570 may further include refining the sensor location. A key characteristic of a sensor, in combination with the sensor's shape, may be used to define the sensor location. For example, a center of mass calculation may be used to determine the center of each identified sensor, and these centers may be regarded as the locations of the sensors. Additionally, the identified locations of the sensors may be ordered to facilitate construction of a suitable curve, as per step 450 of FIG. 4 (for example).

Figure 6:
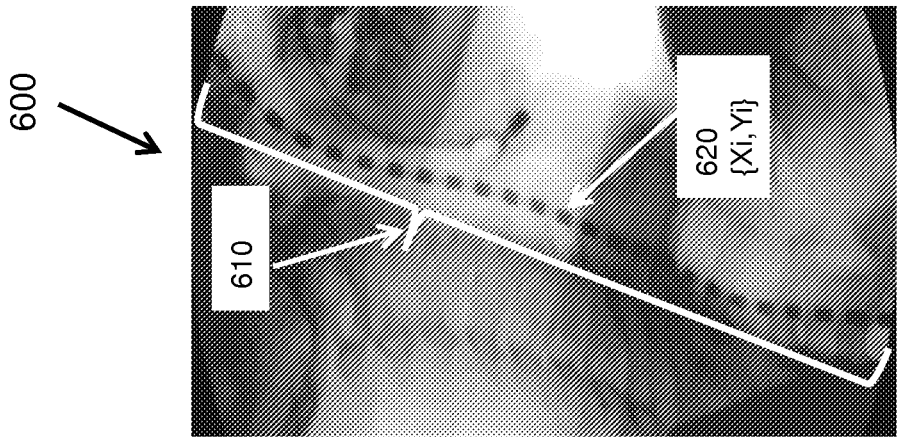
FIG. 6 depicts an example radioscopic image of an organ with a sensor element comprising a set of sensors located along the organ.

FIG. 6 depicts an example radioscopic image 600 of an organ. Shown in radioscopic image 600 is also a sensing element 610 that includes a set of sensors that may be deployed along a body lumen which, in this example, is the pharynx. One sensor is shown at 620 located at location {Xi,Yi}. FIGS. 7, 8 and FIGS. 9A-9B depict radioscopic image 600 and, in addition, three example displayable symbolic representations (color 'ribbon', graph, and filled circles, respectively) that are displayed in spatiotemporal synchronization with the imaged organ. The three displayable symbolic representations are displayed on top of the image of the organ (they may be displayed underneath the image), in relation to the position of the sensors in the image, and the value of the display attributes of the displayable symbolic representations (color in the first instance, distance from a baseline representing the catheter in the second instance, and radius in the third instance) may change from one image to another in compliance with the sensors actual output values associated with each image.

Figure 7:
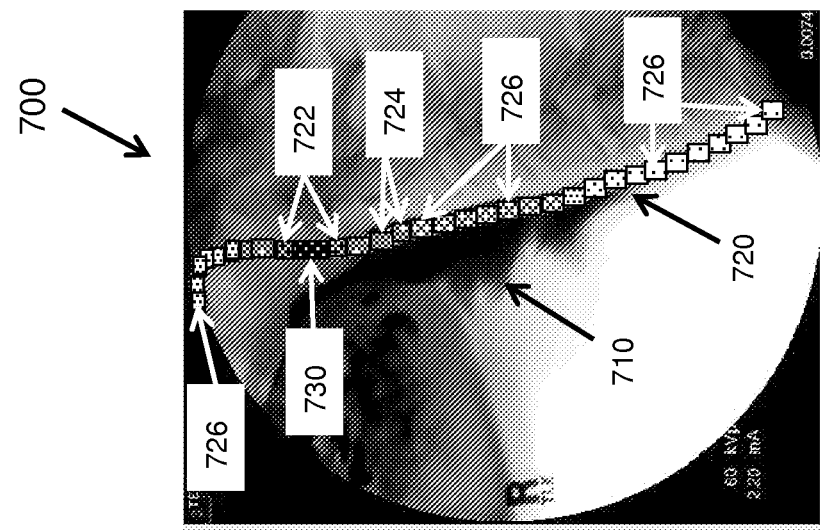
FIG. 7 depicts an example radioscopic image of an organ and physiological data symbolically displayed on top of it according to an example embodiment.

FIG. 7 depicts an example radioscopic image 700 of an organ 710 and physiological data (e.g., pressure data) symbolically displayed on top of it according to an embodiment of the invention. The representation symbol representing the physiological data is shown at 720 as a string of colored rectangles. The colored segments (rectangles) of the ribbon are representatively shown as boxes that contain black dots varying density. For example, the denser the black dots in a box, the redder the box. For example, box 730 may denote a red segment, boxes 722 may denote orange segments, boxes 724 may denote green segments, and boxes 726 may denote blue segments. (The organ itself is shown at 710 as the blackest area delineated by using a contrast bolus.) As a patient swallows (e.g., radio discernible bolus or bolus containing radio contrast material) and the bolus moves down towards, and in, the esophagus by peristaltic pressure while radioscopic images are sequentially acquired (and displayed; e.g., as a video clip), the red box 730, which may represent the maximum peristaltic pressure, may appear to be moving down on a display device, thus visualizing propagation of the peristaltic pressure wave towards to, and along, the studied organ.

Figure 8:
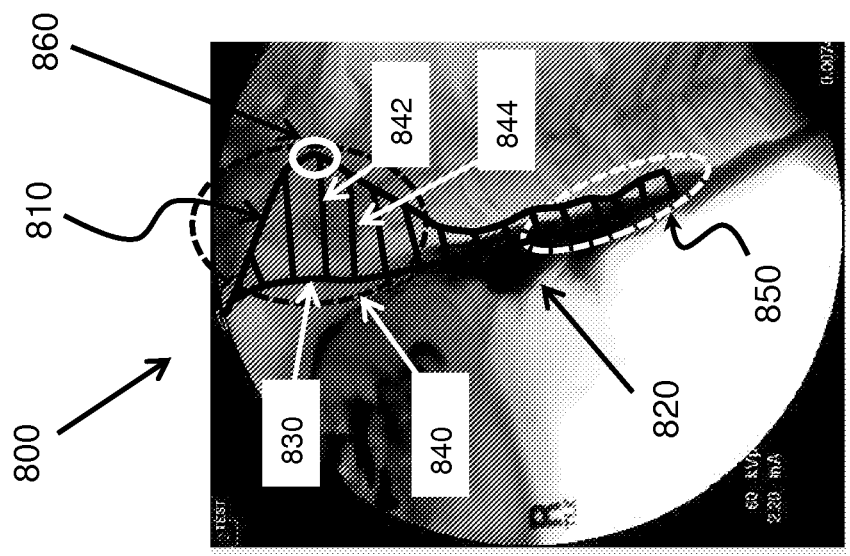
FIG. 8 depicts an example radioscopic image of an organ and physiological data symbolically displayed on top of it according to another example embodiment.

FIG. 8 depicts an example radioscopic image 800 of an organ and physiological data (e.g., pressure data) displayed on top of, or under, it according to another embodiment of the invention. The pressure data may be represented, in this example, by a graph 810, which is an example representation symbol. (The organ itself is shown at 820 delineated by using a contrast material.) Reference numeral 830 denotes a baseline against which, or in relation to which, graph 810 may be constructed. As explained herein, baseline 830 may represent the catheter, or a line occupied by the catheter, in terms of location and shape in the image, because baseline 830 is a curve constructed from (to match) the locations of the sensors residing in, on, or attached to the catheter. By way of example, graph 810 has relatively high values in region 840, which are represented by the graph being relatively distanced away from baseline 830 in this region (two example distances between baseline 830 and graph 810 in region 840 are shown at 842 and 844). By way of example, graph 810 has relatively low values in region 850, which are represented by graph 810 being relatively closer to baseline 830 at this region. Some points on graph 810 are, or represent, the sensors' values, and other points thereon may be obtained by using an interpolation or extrapolation technique, or by using a graph-smoothing algorithm. (Other methods may be used to construct or calculate graph 810.)

Since the points on graph 810 that are, or represent, the sensors' values are spaced apart (to comply with the spacing between the related sensors), then by using a graph such as graph 810, any value of the monitored physiological parameter between any two such points may be estimated. As a patient swallows and the bolus moves down the pharynx by peristaltic pressure while radioscopic images are sequentially acquired (and displayed; e.g., as a video clip), the pressure apex 860 ('pressure' being mentioned as an example parameter, but the parameter can be any type), which may represent the maximum peristaltic pressure, may appear to be moving down (from one image to another) on a display device to visualize the propagation of the peristaltic pressure 'wave' towards to, and along, the studied organ.

FIGS. 9A-9B depict example radioscopic images 900 and 940 of an organ, and physiological data displayed on top of, or under, the radioscopic images according to yet another embodiment of the invention. Referring to FIG. 9A, a series of filled circles, a filled circle per sensor, is shown at 910 distributed along a baseline that may be constructed from, or based on, the locations of the sensors. (The circles are filled, in this example, with black and white squares and the baseline itself is invisible; it is used to position/display the filled circles in the correct locations.) When swallow begins, the values of the peristaltic pressure exerted on the bolus in the entry/upper section of the esophagus may be relatively high, as shown at 920 by the relatively large circles, and relatively low in the lower part thereof, as shown at 930 by the smaller circles. (The greater the size of a circle, the greater the peristaltic pressure represented by it.) For example, circle 922 is greater in size than circle 924 and, therefore, circle 922 represents a peristaltic pressure having a higher value.

FIG. 9B depicts an image 940 that was acquired after image 900. For example, in a series of sequentially acquired images, image 940 may be, for example, the image acquired/taken subsequent to image 900, or it may be the nth (e.g., fifth) image acquired/taken, after image 900. During the swallow process, for example, between the time when image 900 is acquired and the time when image 940 is acquired, the peristaltic pressure (as an example parameter) wave may move along the esophagus. Movement of the peristaltic pressure wave may be visualized across a series of successive images as changes in the instantaneous size of the circles and, if sensors move in the process, also changes in the location of the moving sensors. For example, the instantaneous size of circle 922 in image 900 is greater than its size in image 940, and the instantaneous size of circle 924 in image 900 is smaller than its size in (the subsequent) image 940. When images 900 and 940, and images taken between them, are displayed successively (e.g., as (part of) a video clip), a visual effect may be made, according to which circle 922 and its neighboring circles (e.g., the pressure wave's apex) visually appear to be moving in and along the studied organ in a way that may resemble, represent, reflect, or characterize the dynamics of the studied organ.

Figure 10:
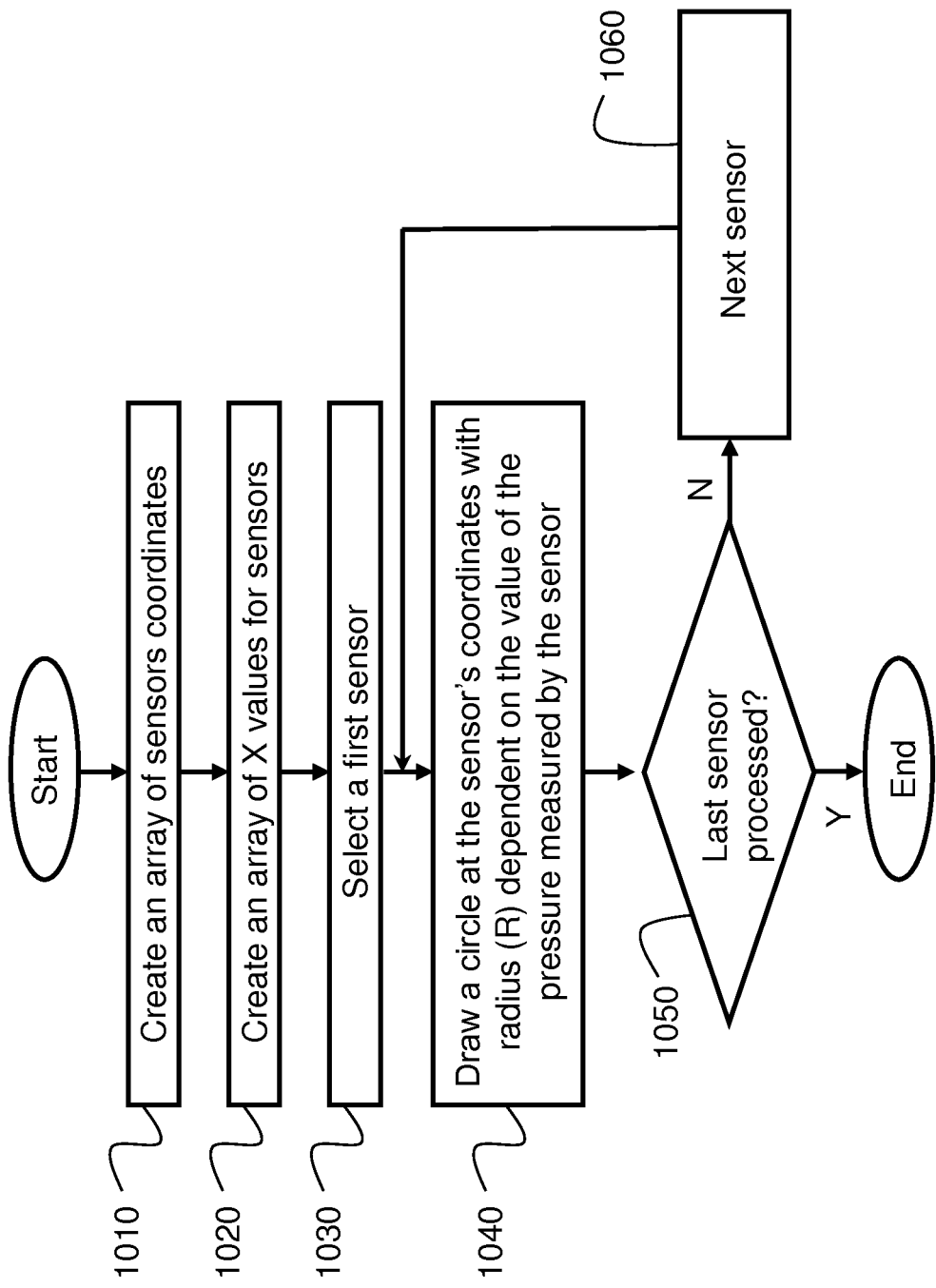
FIG. 10 shows a method for constructing displayable representation of sensor values according to an example embodiment.

FIG. 10 shows a method for constructing filled circles, as an example displayable representation, according to an example embodiment of the invention. FIG. 10 refers to pressure values as read out from the sensors. However, the method of FIG. 10, as well the other methods that are described herein, may likewise be applied to other physiological parameters. At step 1010, an array, or list, of sensors coordinates may be created (e.g., by image processor 140 or processor 170), as per the sensors locations identified in a radioscopic image (e.g., by image processor 140). (Sensors coordinates of unidentified sensors may be inferred, for example by image processor 140 or processor 170, as discussed herein, and then added to the array or list.) At step 1020, an array of instantaneous parameter values (an instantaneous parameter value per sensor) may be created (e.g., by image processor 140 or processor 170) in association with the sensors. (By 'instantaneous parameter value' is meant parameter value that is read out from a sensor's output at the time, or shortly before or after the time, when a radioscopic image is acquired, and 'parameter' may designate, for example, pressure or any other parameter, for example as specified herein; e.g., temperature, EMG, etc.) The array, or list, of sensor coordinates and the array, or list, of sensors' values may be stored in, for example, storage unit 172.

At step 1030, a first sensor may be selected for processing. The selection of a sensor for processing may include selecting the sensor's specific coordinates from the array of sensor coordinates, and selecting the value associated with that sensor from the array of values. At step 1040, a circle may be constructed (its displayable attributes may be set) for the selected sensor such that the circle may be centered at, or adjacent, the sensor's coordinates, and may have a radius, R, whose length may depend on, or derived from, the sensor's output value. By way of example, the radius of a circle may be equal to, for example, one (1.0) plus a scaled value of the value read from, or measured by, that sensor. The circle may be colored using any suitable color that makes it visually conspicuous in the image(s). (The circle may be made visually conspicuous using other methods.)

At step 1050 it is checked whether all the sensors have been processed. If it is determined that there is/are more sensors to process (the condition being shown as 'N' at step 1050), then the next sensor may be selected for processing, at step 1060, and a circle may be constructed for that sensor in a similar way. If, however, it is determined that all the sensors have been processed (the condition being shown as 'Y' at step 1050), the circles construction process may be terminated. Each data that represents a sensor's value may be time stamped by a synchronization unit identical or similar to synchronization unit 181 of FIG. 1B in order to accommodate for differences in the latencies involved in the generation and processing of image data stream and the sensors' data stream.

Figure 11:
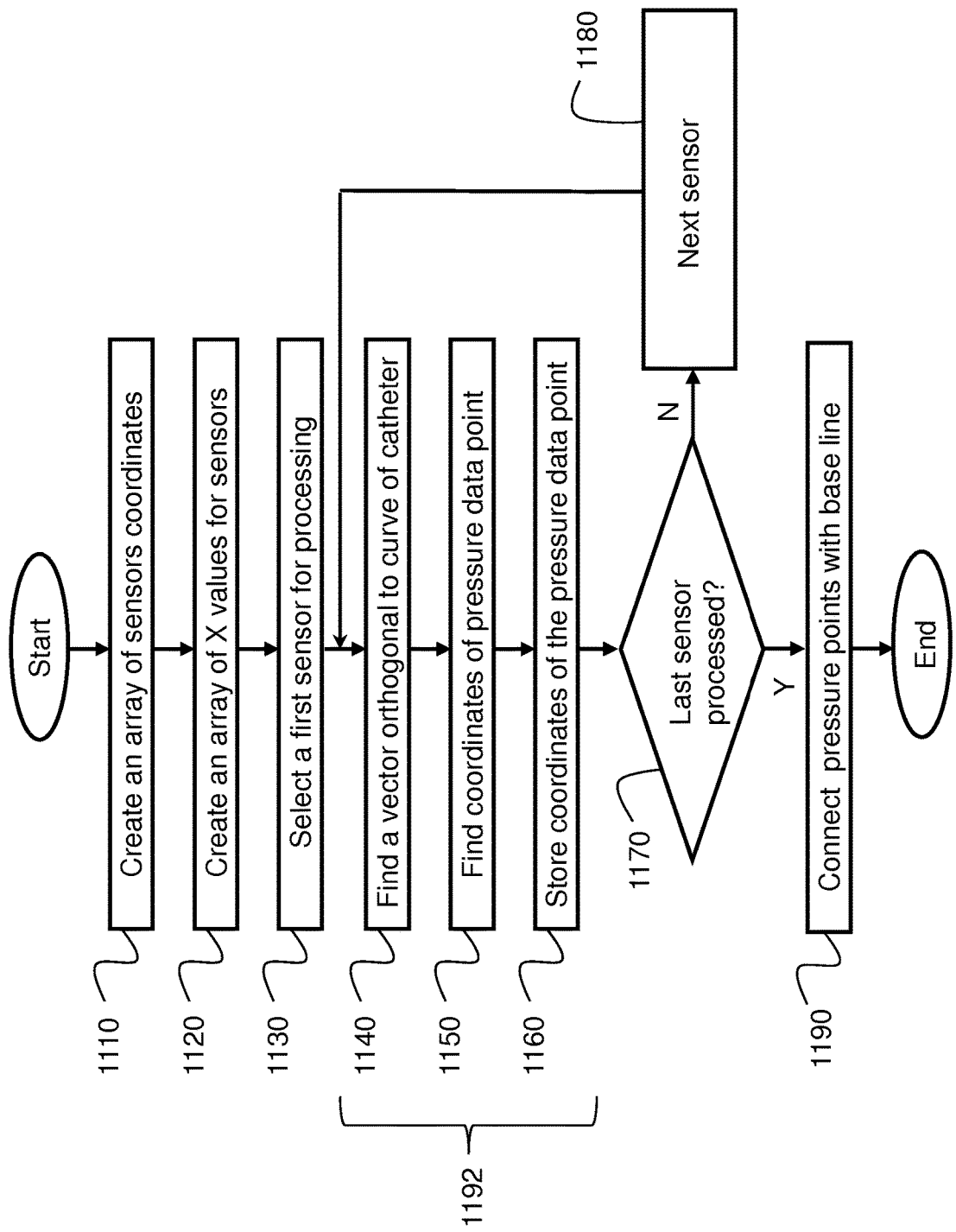
FIG. 11 shows a method for constructing displayable representation of sensor values according to another example embodiment.

FIG. 11 shows a method for constructing a graph according to another example embodiment of the invention. At step 1110, an array, or list, of sensors coordinates may be created (e.g., by image processor 140 or processor 170), as per the sensors locations identified in a radioscopic image (e.g., by image processor 140). (Sensors coordinates of unidentified sensors may be inferred, for example by image processor 140 or processor 170, as discussed herein, and then added to the array or list.) At step 1120, an array of instantaneous parameter values (an instantaneous parameter value per sensor) may be created (e.g., by image processor 140 or processor 170) in association with the sensors. (By 'instantaneous parameter value' is meant parameter value, or output value, that is read out from, or measured by, a sensor at the time, or shortly before or after the time, when a radioscopic image is acquired, and 'parameter' may designate, for example, pressure or any other parameter, for example as specified herein; e.g., temperature, EMG, etc.) The array, or list, of sensor coordinates and the array, or list, of sensors' values may be stored in, for example, storage unit 172.

At step 1130, a sensor may be selected for processing. The selection may include selecting the sensor's specific coordinates from the array/list of sensor coordinates, and the parameter value associated with that sensor from the array/list of parameter values. At step 1140 a vector may be created/calculated such that its origin (a proximal point of the vector) may coincide with, or be adjacent to, a point representing the location of the sensor on the baseline representing the catheter, and a distal point of the vector defines a leg that is orthogonal to that line in that point. At step 1150, coordinates of a data point corresponding to the associated sensor's output value may be calculated. The coordinates of a data point may be calculated, for example, such that the data point spatially coincides with the vector's distal point, and its coordinates are those of the sensor plus a length of a normalized orthogonal that may be multiplied by a scaled value of the sensor's output value. (A scaled value of a parameter value read from a sensor may be obtained, for example, by multiplying the read parameter value by a scale factor; e.g., 0.85.) At step 1160, the coordinates of the data point may be stored.

At step 1170 it is checked whether all the sensors have been processed. If it is determined that there is another sensor to process (the condition being shown as 'N' at step 1170), then another sensor may be selected, at step 1180, for processing, and process 1192 may be repeated for the other sensor. If, however, it is determined that all the sensors have been processed (the condition being shown as 'Y' at step 1170), then, at step 1190, the stored coordinates of the data points may be used to construct a graph similar to graph 223 of FIG. 2F or to graph 810 of FIG. 8.

Figure 12:
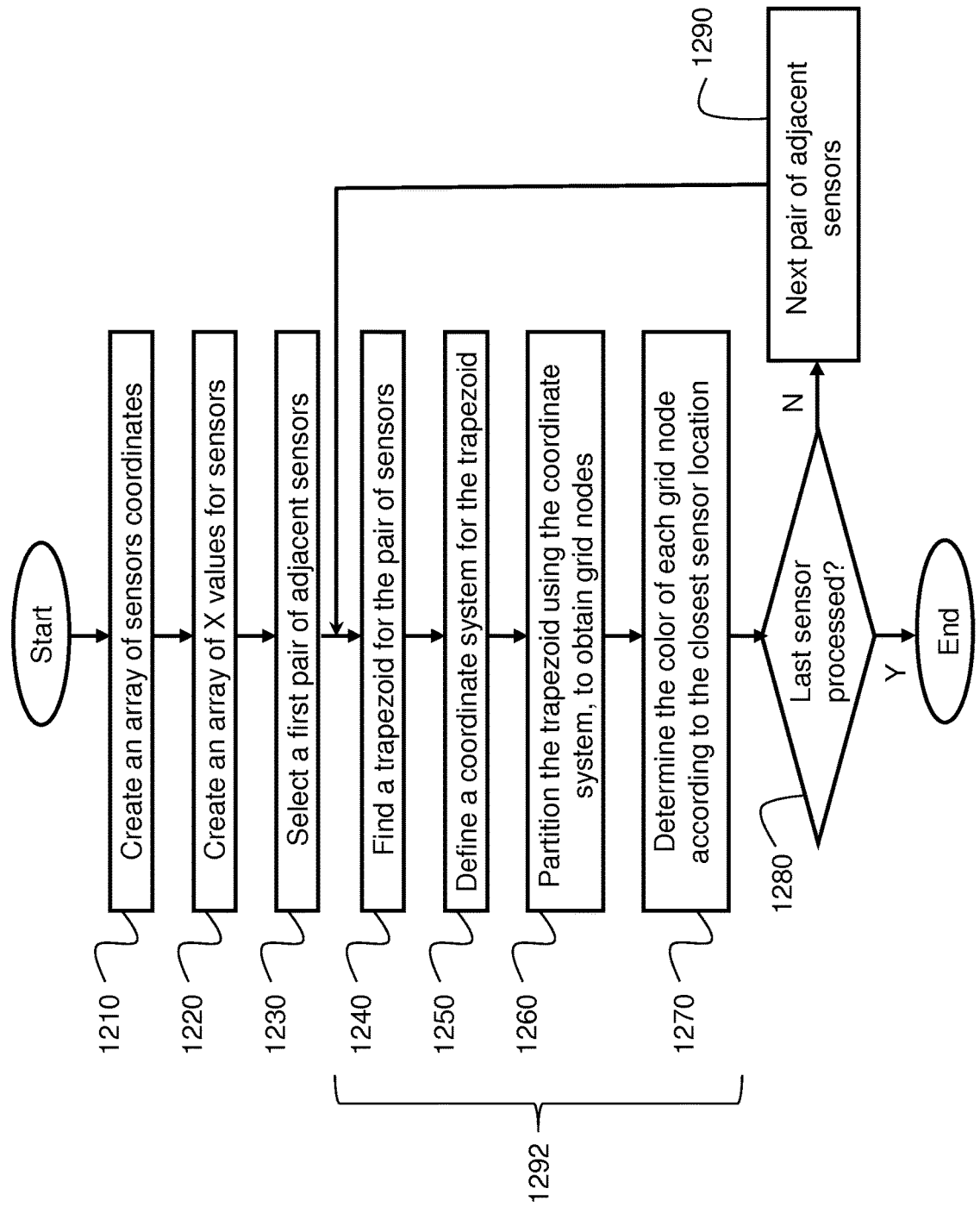
FIG. 12 shows a method for constructing displayable representation of sensor values according to yet another example embodiment.
Figure 13:
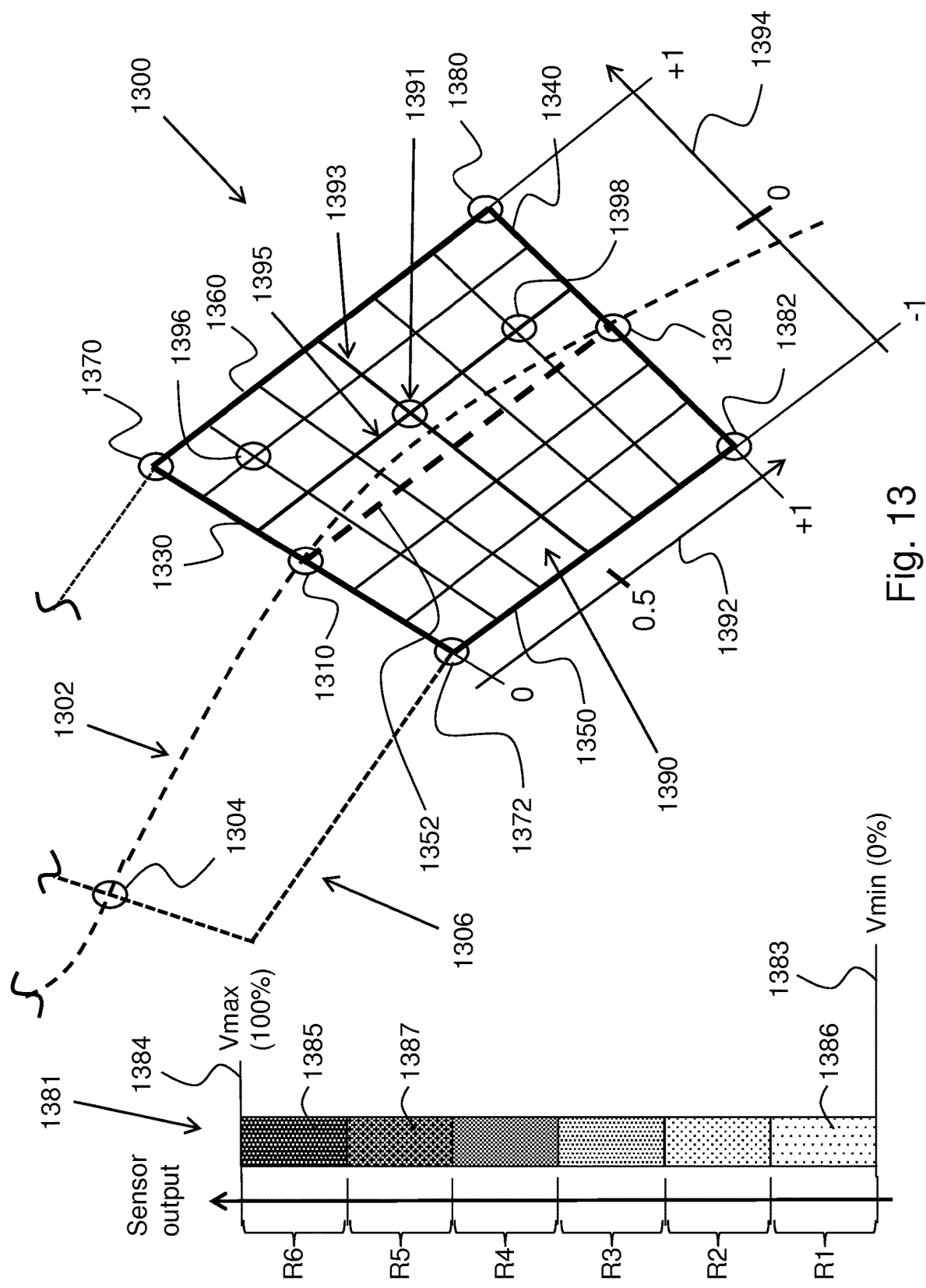
FIG. 13 schematically illustrates creation of graphical elements according to the method shown in FIG. 12.

FIG. 12 shows a method for constructing a colored bar/ribbon according to another example embodiment of the invention. FIG. 12 is described below in association with FIG. 13. Step 1210 and step 1220 may respectively be similar to steps 1010 and 1020 of FIG. 10, or to steps 1110 and 1120 of FIG. 11. At step 1230, a pair of adjacent sensors may be selected for processing. The selection of the pair of adjacent sensors may include selecting the sensors' coordinates from the array/list of sensor coordinates and the output values respectively associated with these sensors from the array/list of pressure values. The selected sensor locations may be used as base points, based on which a quadrilateral object (e.g., trapezoid) may be constructed for this pair of sensors, and the selected output values of these sensors may be used to determine the color of nodes of a grid system which is delimited within, or circumscribed by, the boundaries of the trapezoid. (The method of creating trapezoids and assigning colors the grid nodes is described below in connection with FIG. 13.)

Sensor baseline 1302 is a line connecting the sensors identified and inferred locations in the related radioscopic image. Baseline 1302 may be visible or invisible, a straight line or a curved line. At step 1240, a trapezoid 1300, an example quadrilateral object, may be constructed or calculated for the pair of adjacent sensor locations 1310 and 1320. Trapezoid 1300 may be constructed by perpendicularly extending the trapezoid lateral sides, or legs, from baseline 1302, and constructing or calculating the trapezoid parallel sides, or bases, 1350 and 1360 as lines that may be parallel to a straight line 1352 that connects the two adjacent sensor locations 1310 and 1320. One leg of trapezoid 1300 (e.g., leg 1330) may perpendicularly extend from sensor baseline 1302 at sensor location 1310, and another leg of trapezoid 1300 (e.g., leg 1340) may perpendicularly extend from sensor line 1302 at sensor location 1320. The coordinates of trapezoid corners 1370 and 1372, which delimit, or define, leg 1330, may be determined such that the corners lie on leg 1330 and are oppositely and equidistantly positioned with respect to sensor location 1310. Likewise, the coordinates of corners trapezoid 1380 and 1382 may be determined such that the corners lie on leg 1340, and are oppositely and equidistantly positioned with respect to sensor's location 1320. ('Oppositely positioned' means positioned on either side of sensor location 1310 and sensor location 1320, respectively.)

After trapezoid 1300 is constructed for sensors' locations 1310 and 1320, a coordinate system 1390 may be defined for the trapezoid at step 1250, and, at step 1260, the trapezoid may be partitioned by a grid to obtain grid nodes, the location of each node being definable using the coordinate system. For example, the grid of coordinate system 1390 may span between, for example, grid delimiters 0 and +1.0 (as shown at 1392) in a direction from sensor location 1310 to sensor location 1320, and between grid delimiters −1.0 and +1.0 (as shown at 1394) in a direction that is generally perpendicular to line 1352. The grid lines may be calculated between these grid delimiters, and include nodes such as those shown, for example, at 1396 and 1398.

At step 1270, the distance between each grid node, or of selected grid nodes, within trapezoid 1300 and the location of each of sensor locations 1310 and 1320 may be determined/calculated, and each grid node, or selected grid nodes, may be assigned a color based on its/their closeness to the sensor locations. For example, grid node 1396 of grid system 1390 is closer to sensor location 1310 than to sensor location 1320. Therefore, grid node 1396 may be assigned a color (e.g., red) that is associated with, or determined by, the value of the sensor located at location 1310. In another example, grid node 1398 is closer to sensor location 1320 than to sensor location 1310. Therefore, grid node 1398 may be assigned a color (green) that is associated with, or determined by, the value of the sensor located at location 1320. This means that some area of the trapezoid may have one color (a color associated with or determined by the value of the sensor located at location 1310), whereas the other area of the trapezoid may have a different color (a color associated with or determined by the value of the sensor located at location 1320). (Changes in the output values of the sensors over time may, therefore, result in corresponding changes in the colors of trapezoids.)

At step 1280 it is checked whether all the sensors were processed. If it is determined that there is a sensor that has not been processed yet (the condition being shown as 'N' at step 1280), then a next pair of adjacent sensors may be selected, at step 1290, and the process 1292 may be repeated with respect to this pair of sensors. In ordered sensors, each sensor, with the exception of the first sensor and the last sensor, may be located adjacent to two sensors (it may have one sensor on each side). For example, sensor location 1310 may be adjacent to sensor location 1320 and also to a sensor location 1304. Therefore, sensor location 1310 may be paired with sensor location 1320 to obtain trapezoid 1300, and with sensor location 1304 to obtain a second trapezoid (e.g., trapezoid 1306). Other sensor locations may likewise be used to construct additional trapezoids, thus constructing a series of contiguous trapezoids, a trapezoid per pair of adjacent sensor locations (or adjacent sensors), and the trapezoids may be displayed (e.g., on display device 192) along a line whose shape may resemble the line connecting the sensor locations (e.g., line 1302). The trapezoids may be displayed contiguously and seamlessly because each two adjacent trapezoids have one leg in common. For example, trapezoids 1300 and 1306 have leg 1330 in common.

A grid node may be assigned a color as described above; namely, by searching for the sensor location nearest to the grid node, and assigning to the grid node a color representative of the output value of the related sensor. A grid node may, however, be assigned a color using a different method. For example, a value may be extrapolated for each grid point of a trapezoid from the output values of the sensors used to construct the trapezoid. Extrapolating a value for a grid node may be performed based on a distance D1 between the grid node and one of the two sensor locations used to construct the trapezoid, and on a distance D2 between the grid node and the other sensor location, for example based on the ratio Rd=D1/D2. (The closer a grid node is to a particular sensor location, the closer is the extrapolated value of the node to the output value of the related sensor.) After the extrapolated value is calculated for a particular grid node, a color corresponding to the extrapolated value (a 'conjugated color'), which may be selected; e.g., from a color scale, may be assigned to the grid node.

Assume that a color scale 1381 represents a sensor output value between a minimum value, Vmin (shown at 1383 also as 0%), and a maximum value, Vmax (shown at 1384 also as 100%). By way of example, color scale 1381 may be divided into 6 distinct colors that change, for example, from red (shown at 1385) to blue (shown at 1386). (The color at 1387 may be 'less' red than red color 1385, for example it may be light red, pale red, or yellow. Other colors may be used instead or in addition to those mentioned herein.) Also assume that the sensor output range (Vmin-Vmax) is divided into six sub-ranges, R1, R2, R3, R4, R5 and R6 respectively corresponding to, or represented by the six distinct colors 1385, 1386, 1387, etc. of color scale 1381. Each sub-range, Ri, may be associated, conjugated or paired with, or mapped to, a particular color of the color scale 1381. For example, sub-range R1 may be associated with color 1386, sub-range R5 may be associated with color 1387, and so on.

An extrapolated value, Vext, may be calculated for grid node 1391 as described below. Assume that the output values of the sensors whose locations are 1310 and 1320 are, respectively, V1 and V2, where Vmin<V1<V2<Vmax. Since grid node 1391 is equally distanced from sensor locations 1310 and 1320 (in which case Rd=1 because D1=D2), it may be decided that Vext is the average of the sensors' output values V1 and V2 (Vext=(V1+V2)/2). The color to be assigned to the grid node may, then, be selected according to the sub-range, Ri, within which Vext falls. For example, if Vext falls within sub-range R5, the color assigned to the grid node 1391 is the color 1387 (e.g., light red), which is the color conjugated with sensor value sub-range R5.

All the grid nodes lying on a grid line that is perpendicular to baseline 1302 may have the same color (because the node's distance ratio Rd=D1/D2 is maintained for these nodes), and the color of grid nodes lying on a grid line that is orthogonal to a perpendicular grid line may vary contingent on the node's distance ratio Rd=D1/D2. For example, all the grid nodes lying on perpendicular grid line 1393 may have the same color assigned to grid node 1391 (because the node's distance ratio Rd is equal to 1; i.e., D1=D2, for all these nodes, and the color of grid nodes lying on orthogonal grid line 1395 may vary contingent on changes in the node's distance ratio Rd=D1/D2. For example, the node distance ratio Rd=D1/D2 for node 1398 may be equal (approximately) to 6, with D1 being the (longer) distance between node 1398 and sensor location 1310 and D2 being the distance between node 1398 and sensor location 1320. Assuming that V1 and V2 are, respectively, the values of the sensors at 1310 and 1320, and given the node distance ratio Rd=6 above, then the extrapolated value, Vext, of node 1398 may be calculated, for example, by using the formula Vext=(1/7)×V1+(6/7)×V2. Then, a conjugated color may be selected from color scale 1381 and assigned to node 1398. Other grid nodes may be colored in a similar way. Using the nodes coloring method disclosed herein, or similar methods, is beneficial because color of the resulting color bar/ribbon changes gradually and seamlessly from one sensor to another.

Figure 14:
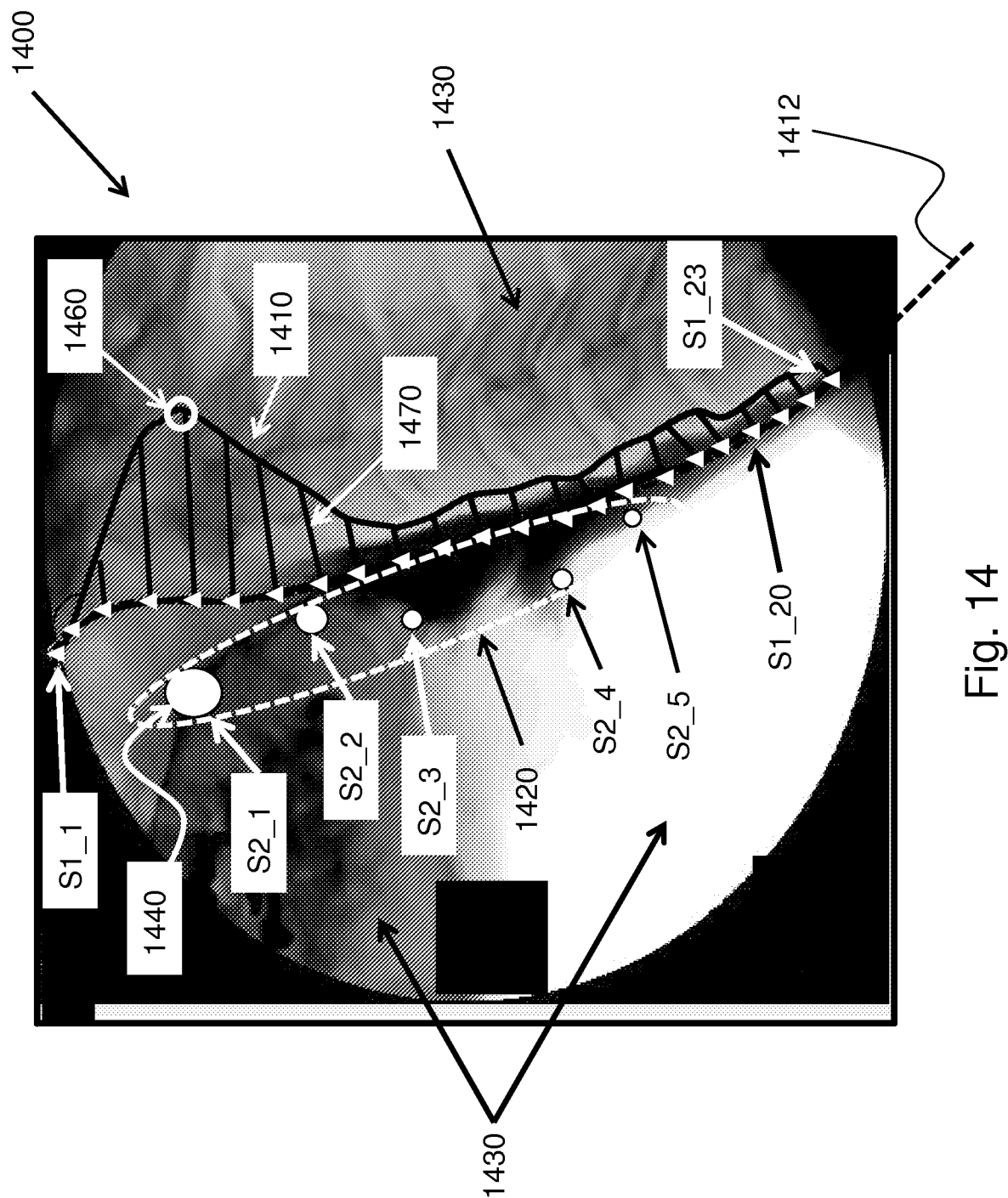
FIG. 14 depicts multiple physiological parameters atop a radioscopic image according to an example embodiment.

FIG. 14 depicts a radioscopic image 1400 of a bodily organ that is overlaid by, or transparently overlaying, two, spatiotemporally synchronized, representation symbols 1410 and 1420 that may be associated with two sensing elements or with two different types of parameters according to an example embodiment of the invention. The imaged bodily organ is shown in radioscopic image 1400 as a low radiographic intensity area (black area)—it has low radiographic intensity values relatively to the imaged background 1430. Each of representation symbols 1410 and 1420 may be constructed for a different type of sensors, and, therefore it may represent a different type of parametric data. For example, representation symbol 1410, which in this example is a graph, may be constructed for a first set of sensors that may be inserted into an organ using a catheter. The first set of sensors may be, for example, pressure sensors, and it may include, for example, 23 sensors, the example locations of which are shown in FIG. 14 at S1_1, S1_2, S1_3, . . . , S1_22, and S1_23. (The locations of sensors S1_1 to S1_23 in image 1400 are symbolically shown as white triangles, but they need not be triangles or white.) There may be more than 23 sensors, or fewer, for which representation symbol 1410 may be constructed. There may be more than two sensing elements or more than two types of parameters, and a visually distinct displayable representation symbol may be constructed for each sensing element, or for each type of parameter, using the methods disclosed herein, or similar methods.

As explained herein, a representation symbol may be biased with respect to the baseline connecting the related sensor locations. Referring to graph 1410, a line representing zero output value of the sensors (that line is referred to herein as 'zero line') may lengthwise equally be distanced away from baseline 1412, and graph 1410 may be constructed with respect to the zero line. In other words, a zero line, with respect to which a representation symbol may be constructed, may coincide with a baseline, which is the line connecting the sensor locations in an image, or be spaced apart therefrom, as discussed herein. The further a graph point is from the baseline or from the zero line, the higher is the pressure measured by the related pressure sensor (if the graph point is an exact point), or estimated/inferred (if the graph point is interpolated).

Representation symbol 1420 may be constructed for, for example, a second set of sensors The second set of sensors may be, for example, temperature sensors, and it may include, for example, 5 sensors, the example locations of which are shown in FIG. 14 at S2_1, S2_2, S2_3, S2_4 and S2_5. There may be more than 5 sensors, or fewer, for which representation symbol 1420 may be constructed. (The locations of sensors S2_1 to S2_5 in image 1400 are symbolically shown as white circles, but they need not be circles or white.) The size (e.g., radius) of each graphical element that make up representation symbol 1420 (e.g., graphical element 1440) may depend on, or be a function of, the temperature measured by the respective temperature sensor.

Representation symbols 1410 and 1420, and possibly additional one or more representation symbols of various types that are not shown in FIG. 14, may all overlay radioscopic image 1400 in spatiotemporal synchronized way. Representation symbol 1420 may be similar to representation symbol 910 of FIGS. 9A-9B in the sense that representation symbol 1420 includes filled circles that respectively represent a set of sensors, where each circle (an example graphical element) may be located at, or adjacent to, the pertinent sensor and sized according to the output value of that sensor. Representation symbol 1410 may be similar to representation symbol 810 of FIG. 8 in the sense that representation symbol 1410 is a graph that represents a set of sensors by being located at a distance from line 1412 that may represent the location of the sensors, and by having data points thereon that represent, or correspond, to the output values of the sensors.

A user interface such as user interface 171 may enable a user to manipulate any representation symbol or to substitute one representation symbol by another. Manipulation of a representation symbol may include, for example, clicking a mouse on a representation symbol (or on a graphical element thereof) to make it temporarily disappear (e.g., for five seconds), clicking a mouse on a displayed graphical element to display its display attributes, momentarily (e.g., for five seconds) moving the representation symbol or a graphical element thereof, changing a display attribute of the representation symbol or of a graphical element thereof, restructuring the representation symbol with a different baseline (e.g., straight line or curved line), etc.

Figure 15A:
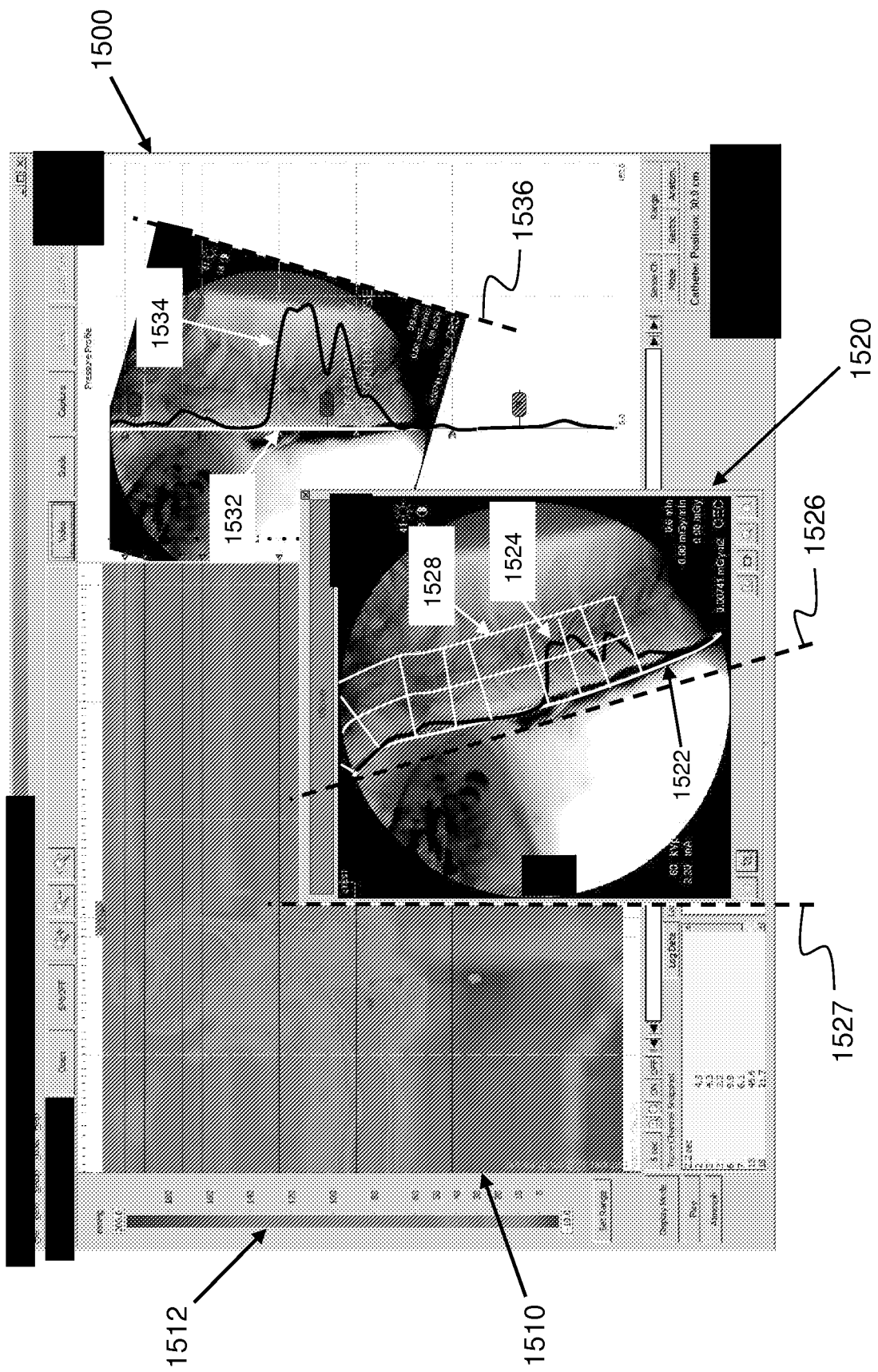
FIGS. 15A-15B depict displayable representation symbol according to another example embodiment.
Figure 15B:
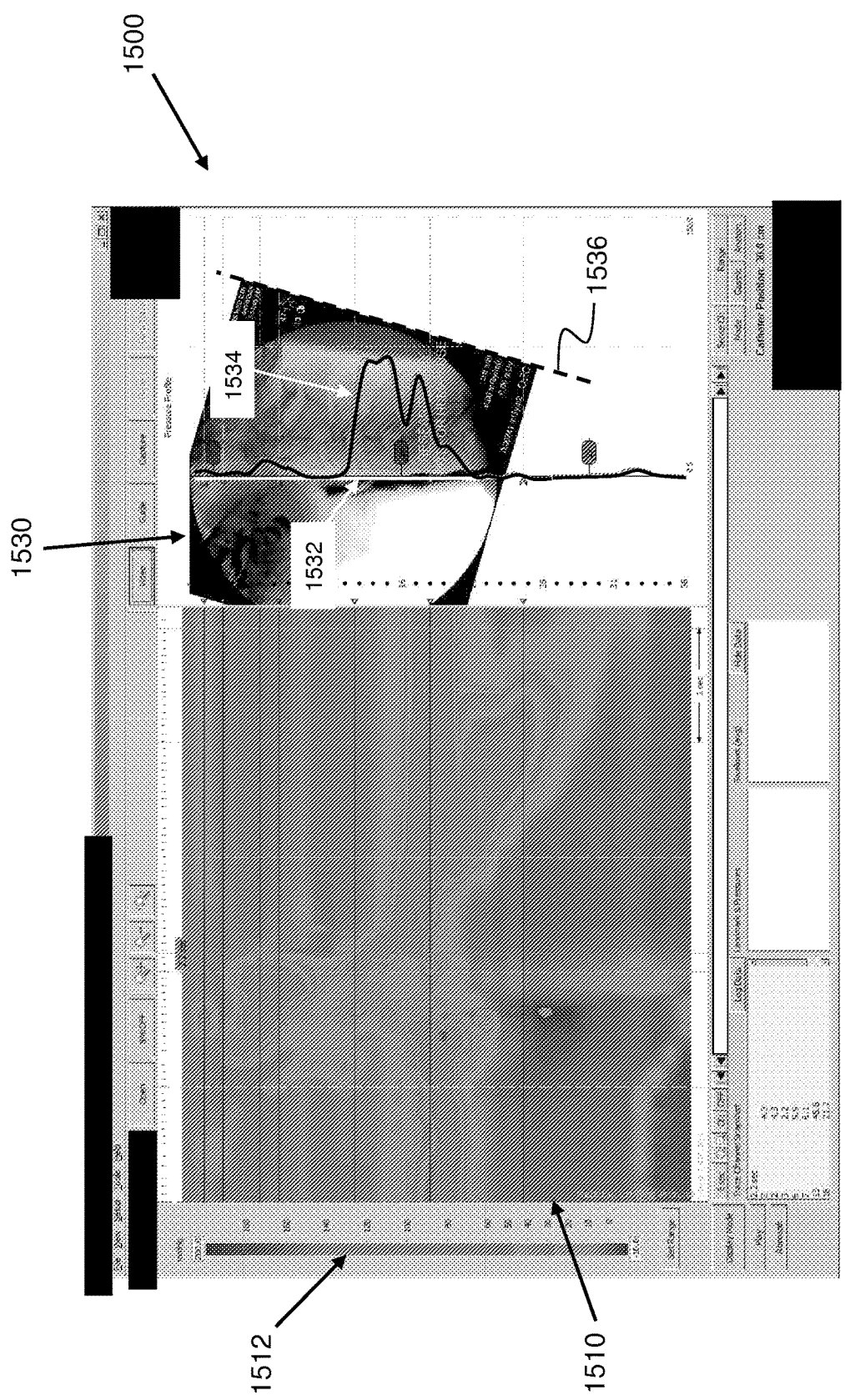

FIGS. 15A-15B depict a user interface 1500 and co-registration of image and related parameter data according to an example embodiment. In this embodiment, the data is displayed in user interface 1500 that allows a user to manipulate the appearance and presentation of a displayed radiographic image, and also the appearance and presentation of data that is related to the displayed radiographic image. The embodiment subject of FIG. 15A uses the ManoView™ software that was developed for displaying various types of data along with a bodily lumen to which the data pertains. User interface 1500 includes three display regions that are displayed in combination: (1) display region 1510, which includes a contour display region 1510, (2) a first radiographic image 1520, and (3) a second radiographic image 1530. Display region 1510 is originally colored, the colors denoting, in this example, pressure values within the range of −10.0 mmHg to +200.0 mmHg, as shown at color scale 1512. (The pressure values were measured in a swallowing system.)

Radioscopic image 1520 includes a radioscopic image of the swallowing system (subject of display region 1510) co-displayed with a 'genuine' representation symbol 1522 that, in this example, is a graph. 'Genuine representation symbol' means a representation symbol (e.g., graph 1522, and possibly an associated isolines system; e.g., isolines 1528) that is positioned in relation to a sensors line (e.g., sensors line 1524) that represents the genuine location, or exact location of each sensor relative to the studied body organ.

Radioscopic image 1520 is superimposed with representation symbol 1522. Representation symbol 1522 may be constructed using the methods disclosed herein, for example in connection with FIG. 9B, or other methods. (In this example representation symbol 1522 is a graph visualizing pressure values.) Line 1524 is a sensors' line, or a baseline, representing the locations of the pressure sensors located along (to measure pressure in different locations of) the studied body lumen. Sensors' line 1524 is noticeably curved at section 1526. Shown at 1528 are isolines, where each isoline denotes a different constant pressure value. Isolines 1528 may be constructed using the methods described herein, or other methods. Image 1520 is shown at a 'normal' viewing orientation (orientation 1523), and sensor's line 1524 is generally shown at an orientation 1525 that, in this example, tilted relative to orientation 1523. Each of sensor's line 1524 and isolines 1528 may be constructed as graphical elements of representation symbol 1522.

Radioscopic image 1530 includes the radioscopic image of the body lumen (subject of display region 1510) co-displayed with a 'non-genuine', or an approximated, representation symbol 1532. Representation symbol 1532 may be constructed in relation to a straight sensors line 1534 that is a linear approximation of, or linearly represents the locations of all the sensors, or at least the locations of some of them. That is, the location of the catheter carrying the sensors, or the location of a line connecting them, may be approximated by a straight line that is referred to herein as a 'sensor location approximating line', which is shown at 1534. Since, in this example, curved section 1526 of sensor line 1524 represents locations of sensors that reside in the nasal cavity, and the information provided by these sensors is relatively less meaningful for the study of swallowing, then using a straight line such as straight line 1534 as a basis for the construction and display of a representation symbol (e.g., representation symbol 1532) is practically satisfactory. Using a straight line such as straight line 1534 to approximate the location and orientation of the sensors, or the catheter (or another instrument) carrying the sensors, is also beneficial because approximating the location and orientation of the sensors in a radiographic image, or in a video clip made from such images, requires knowing the location of only two sensors. Identifying only two sensor locations significantly simplifies the displayable representation symbols construction methods disclosed herein, and enables speeding up the displayable representation symbol construction process. (Even though a straight line may approximate the location of some sensors, the representation symbol still indicates the sensors' real output values.)

Sensors line 1534 is displayed vertically, at an angle relative to sensors line 1524 (or line 1525), and image 1530 and representation symbol 1532 are rotated in unison with sensors line 1534. The rotation angle of sensors line 1534 is, or is approximately, the angle between sensors line 1534 and sensors line 1524 (or line 1525). The rotation angle of radioscopic image 1530 is, or is approximately, the angle between (tilted) line 1536 and (vertical) line 1523. The rotation angle of sensors line 1534 is shown similar to the rotation angle of radioscopic image 1530, but, in general, these rotation angles need not be identical or similar User interface 1500 may include radioscopic image 1520, as demonstrated by FIG. 15A, or not, as demonstrated by FIG. 15B. Radioscopic image 1530 does not have to be rotated with respect to radioscopic image 1520, and straight line 1534 may have the original orientation of baseline 1524 or similar orientation. That is, using a sensor location approximating line such as straight line 1534 may be done without rotating a radioscopic image, and rotating a radioscopic image may be done regardless of the representation symbol or kind of sensor line used (e.g., sensor line representing 'real' catheter position or linearly approximated catheter position).

The articles "a" and "an" are used herein to refer to one or to more than one (e.g., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to".

Different embodiments are disclosed herein. Features of certain embodiments may be combined with features of other embodiments; thus certain embodiments may be combinations of features of other or multiple embodiments. Embodiments of the invention may include an article such as a computer or processor non-transitory storage medium, such as for example a memory, a disk drive, or a USB flash memory, encoding, including or storing instructions, e.g., computer-executable instructions, which when executed by a processor or controller, carry out methods disclosed herein. Some embodiments may be provided in a computer program product that may include a non-transitory machine-readable medium, having stored thereon instructions, which may be used to program a computer, or other programmable devices, to perform methods as disclosed above. Having thus described exemplary embodiments of the invention, it will be apparent to those skilled in the art that modifications of the disclosed embodiments will be within the scope of the invention. Alternative embodiments may, accordingly, include more modules, fewer modules and/or functionally equivalent modules. The present disclosure is relevant to various types of radioscopic imaging, and to various types of sensors and physiological related parameters. Hence the scope of the claims that follow is not limited by the disclosure herein.

The invention claimed is:

1. A method for displaying images of bodily organs and parameters related to the physiological activity of the bodily organs, the method comprising:
   (i) introducing one or more sensing elements into a bodily organ, each sensing element comprising one or more radio discernible sensors, each sensor outputting a signal representative of a physiological parameter associated with the activity of the bodily organ;
   (ii) radioscopically imaging the bodily organ with the one or more sensing elements introduced into the organ, and concurrently reading the output of the sensors of the one or more sensing elements;
   (iii) for each sensing element, visually superimposing the radioscopic image with a displayable representation symbol associated with the sensing element, the representation symbol having display characteristics dependent on the location of the pertinent sensors in the radioscopic image and on the output values of the sensors.

2. The method as in claim 1, comprising constructing the representation symbol for the sensing element by constructing a graphical element for each sensor of the sensing element based on display attributes dependent on the location and output value of the sensor.

3. The method as in claim 2, comprising locating each graphical element at, adjacent or in relation to the location of the pertinent sensor in the radioscopic image, and sizing the graphical element according to the output value of the pertinent sensor.

4. The method as in claim 2, comprising constructing the graphical elements as a single graphical object.

5. The method as in claim 2, comprising constructing the graphical elements individually, as separate graphical objects.

6. The method as in claim 2, wherein the graphical element is selected from the group consisting of: circle, polygon, quadrilateral shaped object, trapezoid, graph, and bar.

7. The method as in claim 6, wherein:
the radius of the circle is a function of the output value of the pertinent sensor;
the quadrilateral object has a color dependent on the output value of the pertinent sensor;
the trapezoid is constructed for a pair of two adjacent sensors based on the related sensors' locations; and
points representing sensor output values are connected to construct the graph.

8. The method as in claim 7, comprising:
dividing the trapezoid by a grid system having grid nodes; and
for each grid node,
calculating a value, Vext, based on distances D1 and D2 of the two adjacent sensors from the grid node and the output values of the adjacent sensors, and
assigning a color to the grid node according to the calculated value Vext.

9. The method as in claim 1, wherein visually superimposing the radioscopic image with the displayable representation symbol associated with the sensing element comprises an action selected from the group consisting of: overlaying the representation symbol on the image and underlying the representation symbol under the image.

10. The method as in claim 1, wherein the representation symbol is selected from the group consisting of: a graph and a color ribbon.

11. The method as in claim 10, wherein constructing the graph comprises connecting data points by a line, the data appoints respectively representing the output values of the sensors, and positioning the line in relation to the sensors locations in the radioscopic image.

12. The method as in claim 1, comprising inferring a location of an unidentified sensor in the radioscopic image from identified locations of sensors.

13. The method as in claim 1, wherein the bodily organ is selected from the group comprising a bodily lumen, pharynx, esophagus, stomach, small bowel, colon, anorectum, and blood vessel.

14. The method as in claim 1, wherein the physiological activity is selected from the group consisting of: peristalsis, swallowing, activity of the stomach, and activity produced by skeletal muscles.

15. The method as in claim 1, wherein a physiological parameter measured by a sensor is selected from the group consisting of: pressure, temperature, acidity (pH), impedance, capacitance, oxygen saturation, Electromyography, and density of a blood constituent.

16. The method as in claim 1, wherein the radio discernible sensors are radiopaque sensors.

17. The method as in claim 1, comprising repeating steps (ii) and (iii) to sequentially produce radioscopic images, and generating an image video from the radioscopic images.

18. A method for displaying images of bodily organs and parameters related to the physiological activity of the bodily organs, the method comprising:
receiving (1) a radioscopic image of a bodily organ with one or more sensing elements introduced into or adjacent to the organ, each sensing element comprising one or more radio discernible sensors, each sensor outputting a signal representative of a physiological parameter associated with the activity of the bodily organ, and (2) output values of the sensors, the sensors output values read at, or shortly before or after, an acquiring time of the radioscopic image;
for each sensing element,
constructing a displayable representation symbol based on display attributes dependent on the location of the sensor element's sensors in the radioscopic image and on the output values of the sensors; and
visually superimposing the radioscopic image with the representation symbol, the representation symbol positioned in relation to the locations of the pertinent sensors in the radioscopic image and having display characteristics corresponding to the output values of the sensors.

19. A system for displaying images of bodily organs and parameters related to the physiological activity of the bodily organs, the system comprising:
a radioscopic imaging system for imaging one or more bodily organs of a patient and one or more sensing elements introduced into the one or more organs, each sensing element comprising one or more radio discernible sensors, each sensor configured to output a signal representative of a physiological parameter associated with the activity of the pertinent bodily organ;
a sensor reading unit for reading the output of the radio discernible sensors;
a computing device configured to,
control the radioscopic imaging system to radioscopically image the one or more bodily organs with the one or more sensing elements, and to control the sensor reading unit to concurrently read the output of the sensors; and
for each sensing element,
to superimpose the radioscopic image with a displayable representation symbol associated with the sensing element's sensors, the representation symbol having display characteristics dependent on the location of the sensors in the radioscopic image and on the output values of the sensors; and
a display device to display the radioscopic image and the displayable representation symbol(s) according to the display characteristics.

20. The system as in claim 19, wherein the computing device is configured to construct a representation symbol for the one or more sensing elements by constructing a graphical element for each sensor of the one or more sensing elements based on display attributes dependent on the location and output value of the sensor.

* * * * *